US010186397B2

(12) United States Patent
Price et al.

(10) Patent No.: US 10,186,397 B2
(45) Date of Patent: Jan. 22, 2019

(54) WORKPIECE HOLDER FOR WORKPIECE TRANSPORT APPARATUS

(71) Applicant: Howard Hughes Medical Institute, Ashburn, VA (US)

(72) Inventors: John H. Price, Hingham, MA (US); Dravida Bock, Ashburn, VA (US)

(73) Assignee: Howard Hughes Medical Institute, Ashburn, VA (US)

( * ) Notice: Subject to any disclaimer, the term of this patent is extended or adjusted under 35 U.S.C. 154(b) by 893 days.

(21) Appl. No.: 14/538,327

(22) Filed: Nov. 11, 2014

(65) Prior Publication Data
US 2015/0166273 A1 Jun. 18, 2015

Related U.S. Application Data

(60) Provisional application No. 61/902,470, filed on Nov. 11, 2013.

(51) Int. Cl.
*H01J 37/20* (2006.01)
*H01J 37/26* (2006.01)
(Continued)

(52) U.S. Cl.
CPC ........ *H01J 37/20* (2013.01); *G01N 35/00732* (2013.01); *H01J 37/023* (2013.01); *H01J 37/185* (2013.01); *H01J 37/261* (2013.01); *G01N 1/32* (2013.01); *H01J 2237/201* (2013.01); *H01J 2237/204* (2013.01); *H01J 2237/2007* (2013.01); *H01J 2237/20278* (2013.01); *H01J 2237/20285* (2013.01);
(Continued)

(58) Field of Classification Search
None
See application file for complete search history.

(56) References Cited

U.S. PATENT DOCUMENTS 4,183,614 A    1/1980  Feldman
4,672,797 A *  6/1987  Hagler ............... G01N 1/28
                                              250/440.11
(Continued)

FOREIGN PATENT DOCUMENTS

WO    9117941       11/1991
WO    2008049133    4/2008
WO    2014003557    1/2014

OTHER PUBLICATIONS

International Search Report, International Application No. PCT/US2014/065030, dated Apr. 1, 2015.

*Primary Examiner* — Isaac T Tecklu
(74) *Attorney, Agent, or Firm* — Perman & Green, LLP

(57) ABSTRACT

An automated workpiece processing system including at least one workpiece processing unit, a workpiece holder configured to removably hold a batch of workpieces therein, each workpiece embodying workpiece identifying indicia where the workpiece identifying indicia is a physical representation of a sample held on a respective workpiece, and to interface with the at least one automated workpiece processing unit, and a controller including a memory having a data structure therein that effects, with the workpiece identifying indicia, batch process tracking of each workpiece in the batch of workpieces through the at least one automated workpiece processing unit in a predetermined batch workpiece processing sequence.

22 Claims, 26 Drawing Sheets

(51) Int. Cl.
  *H01J 37/02* (2006.01)
  *H01J 37/18* (2006.01)
  *G01N 35/00* (2006.01)
  *G01N 1/32* (2006.01)

(52) U.S. Cl.
  CPC . *H01J 2237/20292* (2013.01); *H01J 2237/26* (2013.01); *H01J 2237/2602* (2013.01)

(56) References Cited

U.S. PATENT DOCUMENTS

| | | | |
|---|---|---|---|
| 4,917,556 A | 4/1990 | Stark et al. | |
| 5,124,645 A | 6/1992 | Rhoden | |
| 5,246,524 A * | 9/1993 | Kuroda | H01L 21/67173 118/35 |
| 5,326,971 A | 7/1994 | Theodore et al. | |
| 5,726,433 A | 3/1998 | Peng | |
| 5,753,924 A | 5/1998 | Swann | |
| 5,773,951 A | 6/1998 | Markowski et al. | |
| 5,821,544 A | 10/1998 | Augustus et al. | |
| 6,002,136 A | 12/1999 | Naeem | |
| 6,068,437 A * | 5/2000 | Boje | B65G 1/127 198/346.2 |
| 6,242,737 B1 * | 6/2001 | Ohnishi | B82Y 35/00 250/442.11 |
| 6,258,326 B1 * | 7/2001 | Modlin | B01L 3/5085 422/553 |
| 6,281,510 B1 * | 8/2001 | Yoshitake | H01L 21/67748 250/370.1 |
| 6,388,262 B1 | 5/2002 | Alani | |
| 6,495,838 B1 * | 12/2002 | Yaguchi | H01J 37/20 250/443.1 |
| 6,597,500 B1 * | 7/2003 | Burke | G02B 21/34 359/396 |
| 6,717,156 B2 | 4/2004 | Sugaya et al. | |
| 6,858,851 B2 | 2/2005 | Tomimatsu et al. | |
| 6,872,955 B1 * | 3/2005 | Balcome | H01J 37/20 250/440.11 |
| 6,891,170 B1 | 5/2005 | Yu et al. | |
| 6,902,703 B2 * | 6/2005 | Marquiss | B01L 3/50853 422/505 |
| 6,927,400 B2 * | 8/2005 | Rasmussen | G01N 1/04 250/307 |
| 6,946,654 B2 * | 9/2005 | Gerlach | H01J 37/141 250/306 |
| 6,963,068 B2 * | 11/2005 | Asselbergs et al. | G01N 1/04 250/307 |
| 6,967,335 B1 * | 11/2005 | Dyer | G02B 21/32 250/442.11 |
| 6,995,380 B2 | 2/2006 | Rasmussen | |
| 7,034,316 B2 * | 4/2006 | Wagner | H01J 37/20 250/311 |
| 7,071,475 B2 * | 7/2006 | Tomimatsu | G01N 1/28 250/442.11 |
| 7,074,575 B2 * | 7/2006 | Chandrasekher | A61K 31/337 435/7.2 |
| 7,115,882 B2 * | 10/2006 | Moore | H01J 37/20 250/440.11 |
| 7,126,133 B2 | 10/2006 | Moore | |
| 7,138,628 B2 | 11/2006 | Tomimatsu et al. | |
| 7,230,253 B2 * | 6/2007 | Ham | H01J 37/20 250/442.11 |
| 7,247,864 B2 | 7/2007 | Mito et al. | |
| 7,253,408 B2 * | 8/2007 | West | G01Q 70/02 250/227.26 |
| 7,375,325 B2 * | 5/2008 | Burkhardt | B25J 7/00 250/306 |
| 7,381,968 B2 * | 6/2008 | Tanaka | H01J 37/20 250/310 |
| 7,390,458 B2 * | 6/2008 | Burow | B01L 9/523 414/222.13 |
| 7,474,419 B2 * | 1/2009 | Tappel | H01J 37/20 356/614 |
| 7,476,787 B2 * | 1/2009 | Thomas | G01N 21/6458 250/306 |
| 7,511,282 B2 * | 3/2009 | Agorio | G01N 1/286 216/2 |
| 7,601,272 B2 | 10/2009 | Nguyen et al. | |
| 7,625,679 B2 * | 12/2009 | Sullivan | B82Y 10/00 430/22 |
| 7,644,637 B2 * | 1/2010 | Moore | B25J 21/02 73/863 |
| 7,663,101 B2 * | 2/2010 | Goodman | B01L 3/0275 250/304 |
| 7,675,049 B2 * | 3/2010 | Schmidt | B23K 15/0086 250/306 |
| 7,677,289 B2 * | 3/2010 | Hayworth | G01N 1/06 156/254 |
| 7,745,785 B2 * | 6/2010 | Nishiyama | G01N 23/225 250/306 |
| 7,745,802 B2 * | 6/2010 | Nishiyama | H01J 37/20 250/306 |
| 7,851,769 B2 * | 12/2010 | Schmid | H01J 37/20 250/306 |
| 7,888,655 B2 * | 2/2011 | van Gaasbeek | H01J 37/20 250/442.11 |
| 7,906,762 B2 | 3/2011 | Bierhoff et al. | |
| 7,913,700 B2 * | 3/2011 | Calandro | A24B 15/16 131/352 |
| 7,923,700 B2 * | 4/2011 | Nishiyama | G01N 23/2251 250/309 |
| 7,928,380 B2 * | 4/2011 | Suga | H01J 37/20 250/306 |
| 7,935,937 B2 * | 5/2011 | Moore | H01J 37/20 250/311 |
| 7,939,906 B2 * | 5/2011 | Luo | G01N 1/28 250/304 |
| 7,989,778 B2 | 8/2011 | Oetelaar et al. | |
| 8,011,259 B2 | 9/2011 | Dona | |
| 8,030,622 B2 | 10/2011 | Nishiyama et al. | |
| 8,058,627 B2 | 11/2011 | Zach | |
| 8,102,523 B1 | 1/2012 | Marsh et al. | |
| 8,125,652 B2 | 2/2012 | Fogel et al. | |
| 8,139,213 B2 | 3/2012 | Bahatt et al. | |
| 8,143,593 B2 | 3/2012 | Milas et al. | |
| 8,148,685 B2 | 4/2012 | Qian et al. | |
| 8,164,057 B2 | 4/2012 | Shacal | |
| 8,207,431 B2 | 6/2012 | Feng et al. | |
| 8,222,618 B2 | 7/2012 | Tokuda et al. | |
| 8,227,781 B2 | 7/2012 | Zaykova-Feldman et al. | |
| 8,258,473 B2 | 9/2012 | Shaapur et al. | |
| 8,263,929 B2 | 9/2012 | Nakayama et al. | |
| 8,228,723 B2 | 10/2012 | Zhang et al. | |
| 8,294,098 B2 | 10/2012 | Zhang et al. | |
| 8,309,921 B2 | 11/2012 | Bierhoff et al. | |
| 8,334,510 B2 | 12/2012 | Shachal et al. | |
| 8,336,405 B2 | 12/2012 | Stabacinskiene et al. | |
| 8,346,574 B2 | 1/2013 | Chirica et al. | |
| 8,387,227 B2 | 3/2013 | Liu et al. | |
| 8,395,130 B2 | 3/2013 | Gatcher | |
| 8,410,457 B2 | 4/2013 | Terada et al. | |
| 8,436,303 B2 | 5/2013 | Zhang et al. | |
| 8,439,216 B1 | 5/2013 | Walck | |
| 8,455,821 B2 | 6/2013 | Arjavac et al. | |
| 8,455,842 B2 | 6/2013 | Zhang et al. | |
| 8,497,487 B2 | 7/2013 | Milas et al. | |
| 8,507,876 B2 | 8/2013 | Goodman et al. | |
| 8,524,139 B2 | 9/2013 | Toth et al. | |
| 8,524,450 B2 | 9/2013 | Moon et al. | |
| 8,569,719 B2 | 10/2013 | Tomimatsu et al. | |
| 8,581,205 B2 | 11/2013 | Wei et al. | |
| 8,598,485 B2 | 12/2013 | Adachi | |
| 8,618,520 B2 | 12/2013 | Tokuda et al. | |
| 8,623,227 B2 | 1/2014 | Lin et al. | |
| 8,629,416 B2 | 1/2014 | Straw et al. | |
| 8,639,463 B2 | 1/2014 | Kimba et al. | |
| 8,650,739 B2 | 2/2014 | Qian et al. | |
| 8,653,476 B2 | 2/2014 | Miyazaki | |
| 8,662,392 B2 | 3/2014 | Hagen et al. | |
| 8,676,509 B2 | 3/2014 | De La Torre-Bueno | |
| 8,704,175 B2 | 4/2014 | Sohda et al. | |

(56) References Cited

U.S. PATENT DOCUMENTS

| | | |
|---|---|---|
| 8,716,676 B2 | 5/2014 | Safar |
| 8,742,344 B2 | 6/2014 | Hatakeyama et al. |
| 8,754,384 B1 | 6/2014 | Persoon et al. |
| 9,159,531 B2 | 10/2015 | Nederlof |
| 9,207,196 B2 | 12/2015 | De Jonge |
| 2001/0002986 A1* | 6/2001 | Fattinger .............. B01J 19/0046 422/562 |
| 2002/0028399 A1* | 3/2002 | Nakasuji .............. G01N 23/225 430/30 |
| 2002/0166976 A1 | 11/2002 | Sugaya et al. |
| 2004/0237670 A1* | 12/2004 | Koo ...................... H01J 37/20 73/863 |
| 2004/0256570 A1* | 12/2004 | Wagner .................. H01J 37/20 250/440.11 |
| 2005/0107917 A1* | 5/2005 | Smith .................. B25J 15/0253 700/245 |
| 2005/0200841 A1 | 9/2005 | Talbot et al. |
| 2005/0254064 A1* | 11/2005 | Basler ................ A61C 13/0022 356/601 |
| 2007/0029503 A1* | 2/2007 | Jung ........................ G01N 1/32 250/440.11 |
| 2007/0029504 A1 | 2/2007 | Saito et al. |
| 2007/0207549 A1 | 9/2007 | Sangha et al. |
| 2008/0014056 A1 | 1/2008 | Miller |
| 2008/0068706 A1* | 3/2008 | Goodman ............. B01L 3/0275 359/368 |
| 2008/0250881 A1* | 10/2008 | Dona ...................... H01J 37/20 73/864.91 |
| 2010/0025580 A1* | 2/2010 | Hammer ................ H01J 37/20 250/311 |
| 2010/0230584 A1* | 9/2010 | Niebel .................. H01J 37/153 250/252.1 |
| 2010/0230590 A1* | 9/2010 | Bierhoff ................ H01J 37/16 250/310 |
| 2011/0017922 A1* | 1/2011 | Amador ................ H01J 37/20 250/442.11 |
| 2011/0133065 A1 | 6/2011 | Nakayama et al. |
| 2011/0210250 A1 | 9/2011 | Nakayama et al. |
| 2011/0253905 A1 | 10/2011 | Moebus et al. |
| 2011/0253908 A1 | 10/2011 | Feng et al. |
| 2012/0006711 A1 | 1/2012 | Goodman et al. |
| 2013/0099134 A1 | 4/2013 | Sun et al. |
| 2013/0323829 A1 | 12/2013 | Torterella |
| 2013/0328246 A1 | 12/2013 | Wells et al. |
| 2014/0014835 A1 | 1/2014 | Hosoya et al. |
| 2014/0042338 A1 | 2/2014 | Shibata et al. |
| 2014/0233691 A1 | 8/2014 | Sheppard et al. |

\* cited by examiner

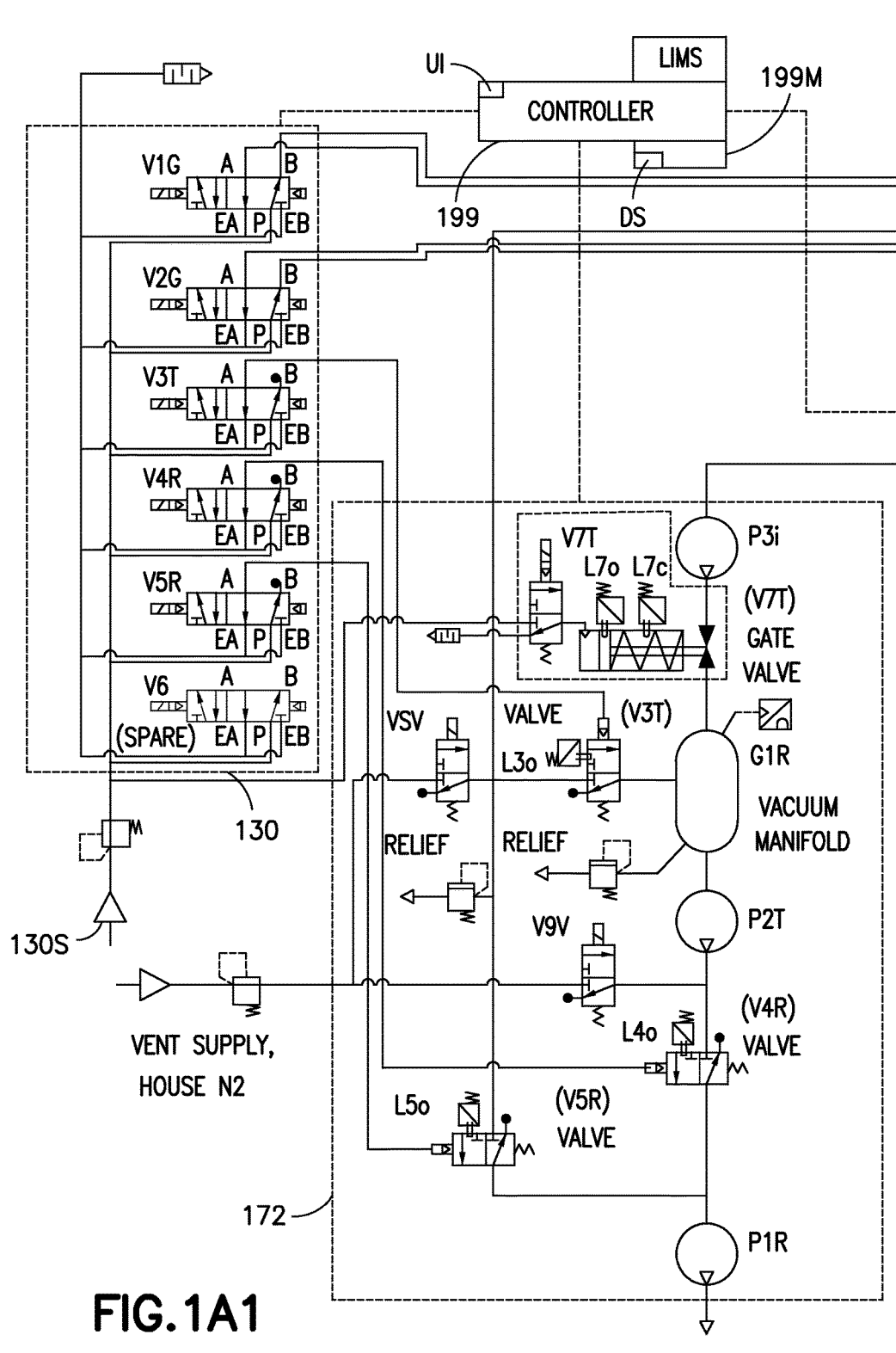
FIG.1A1

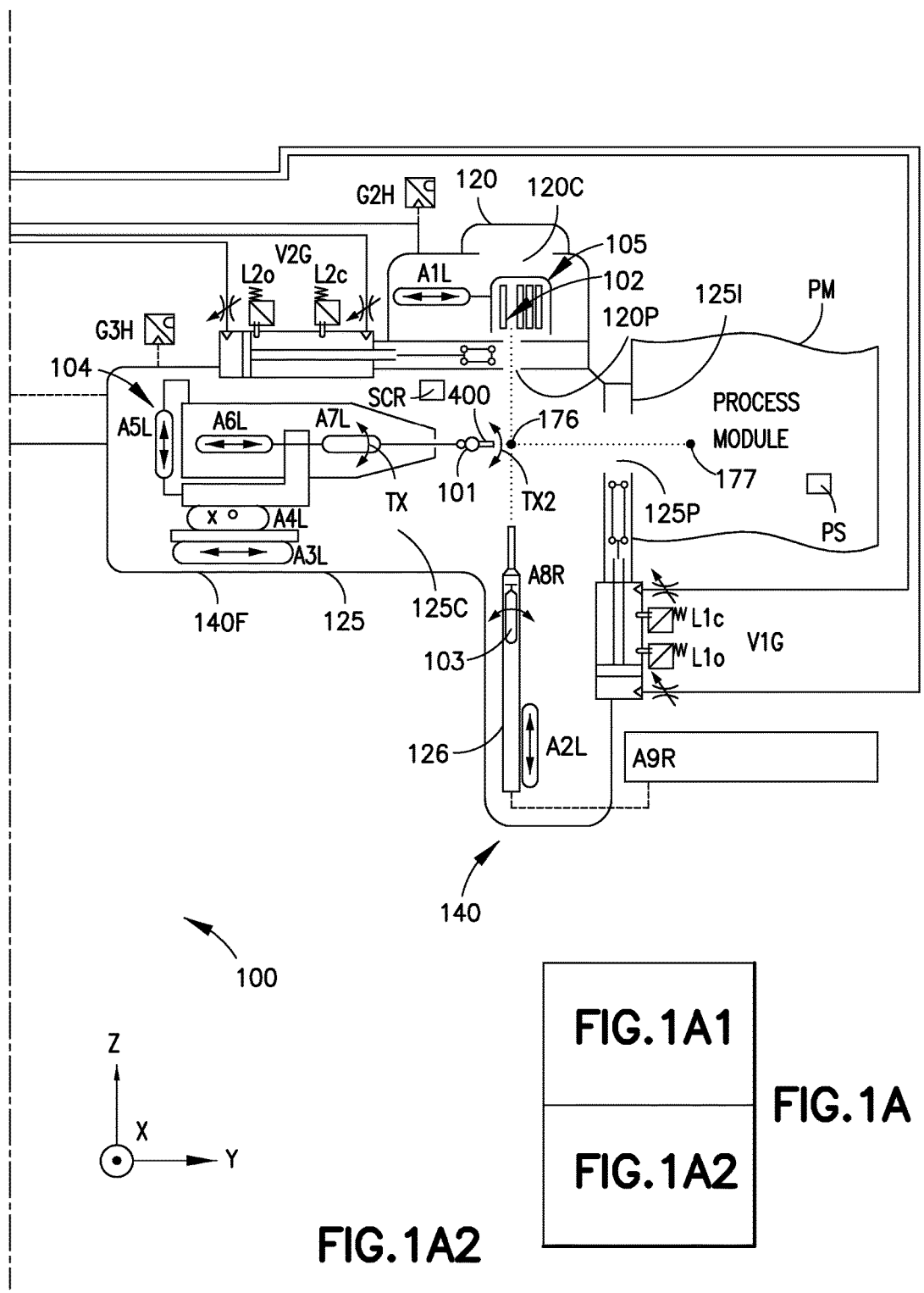
FIG.1A2

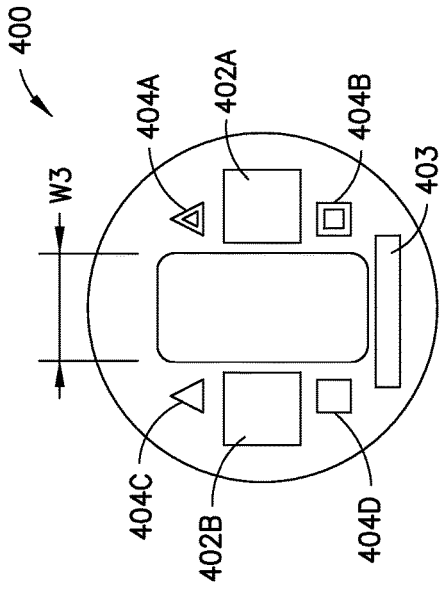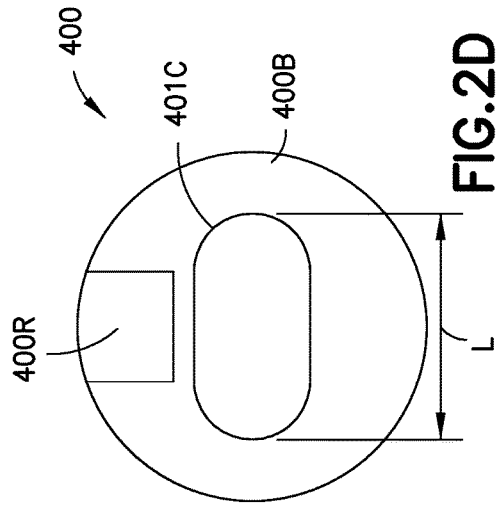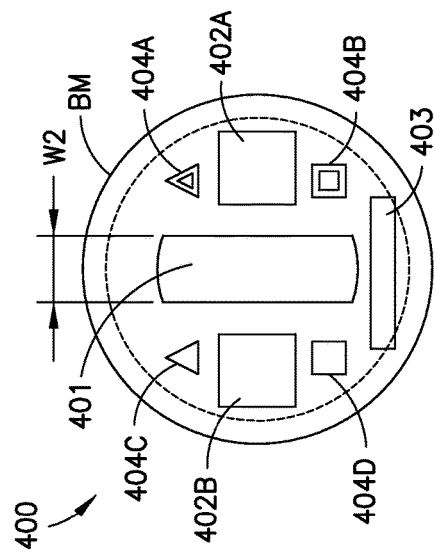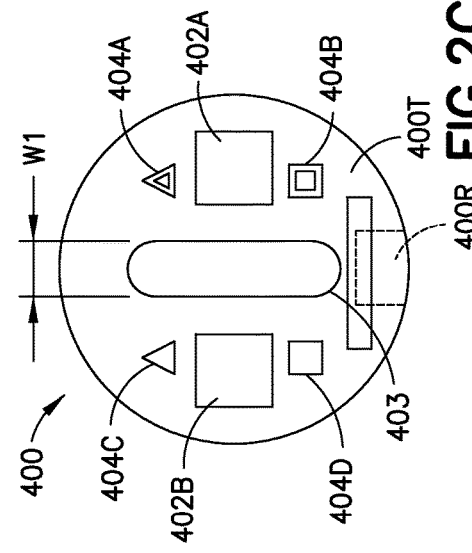

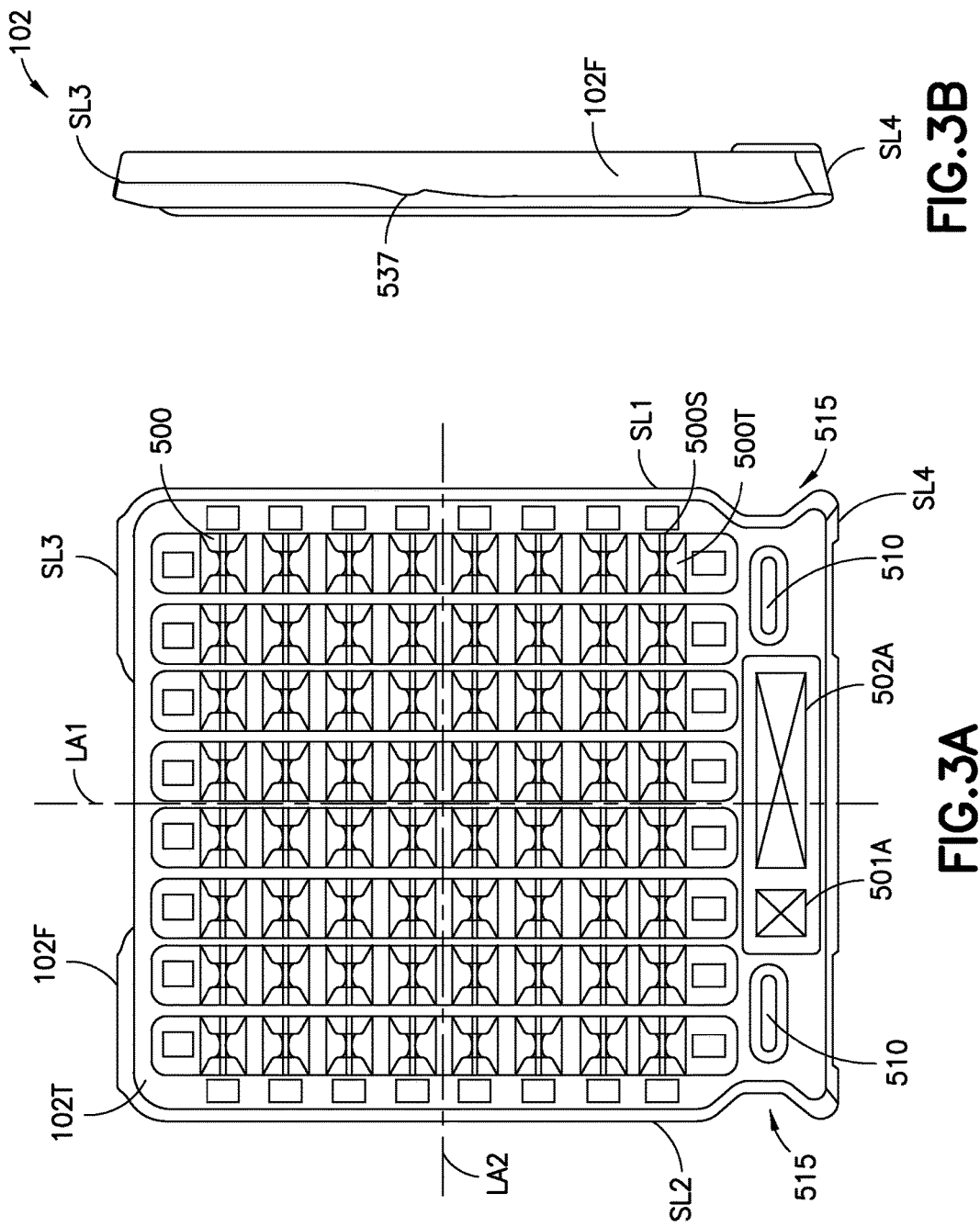

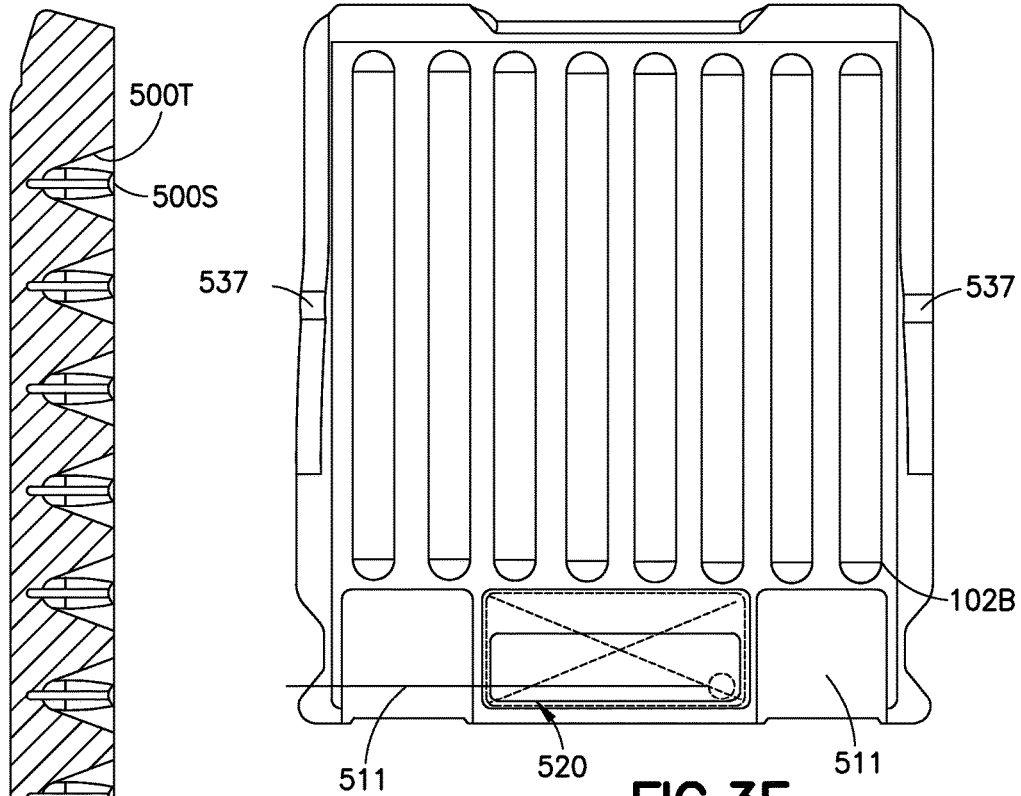
FIG.3F
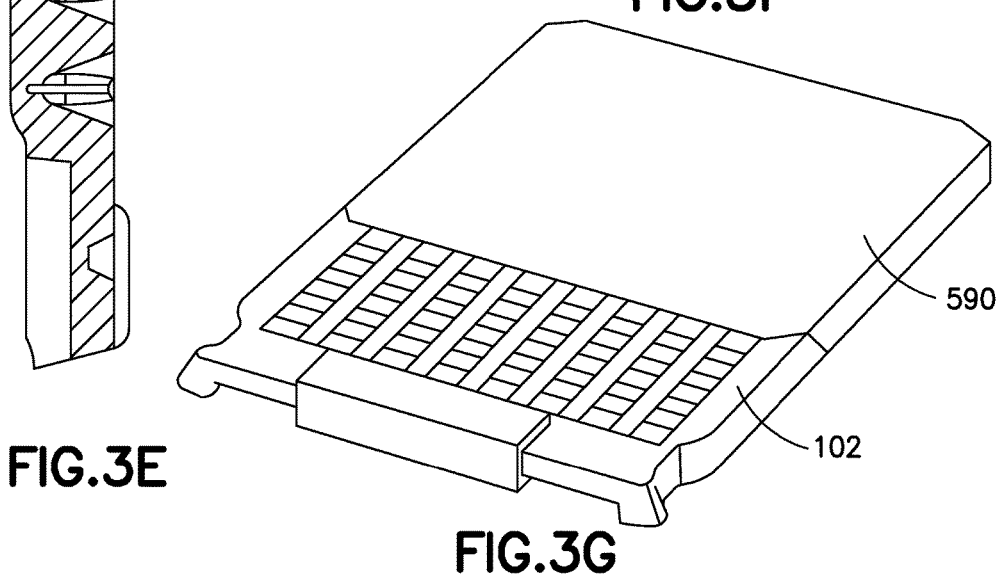
FIG.3E
FIG.3G

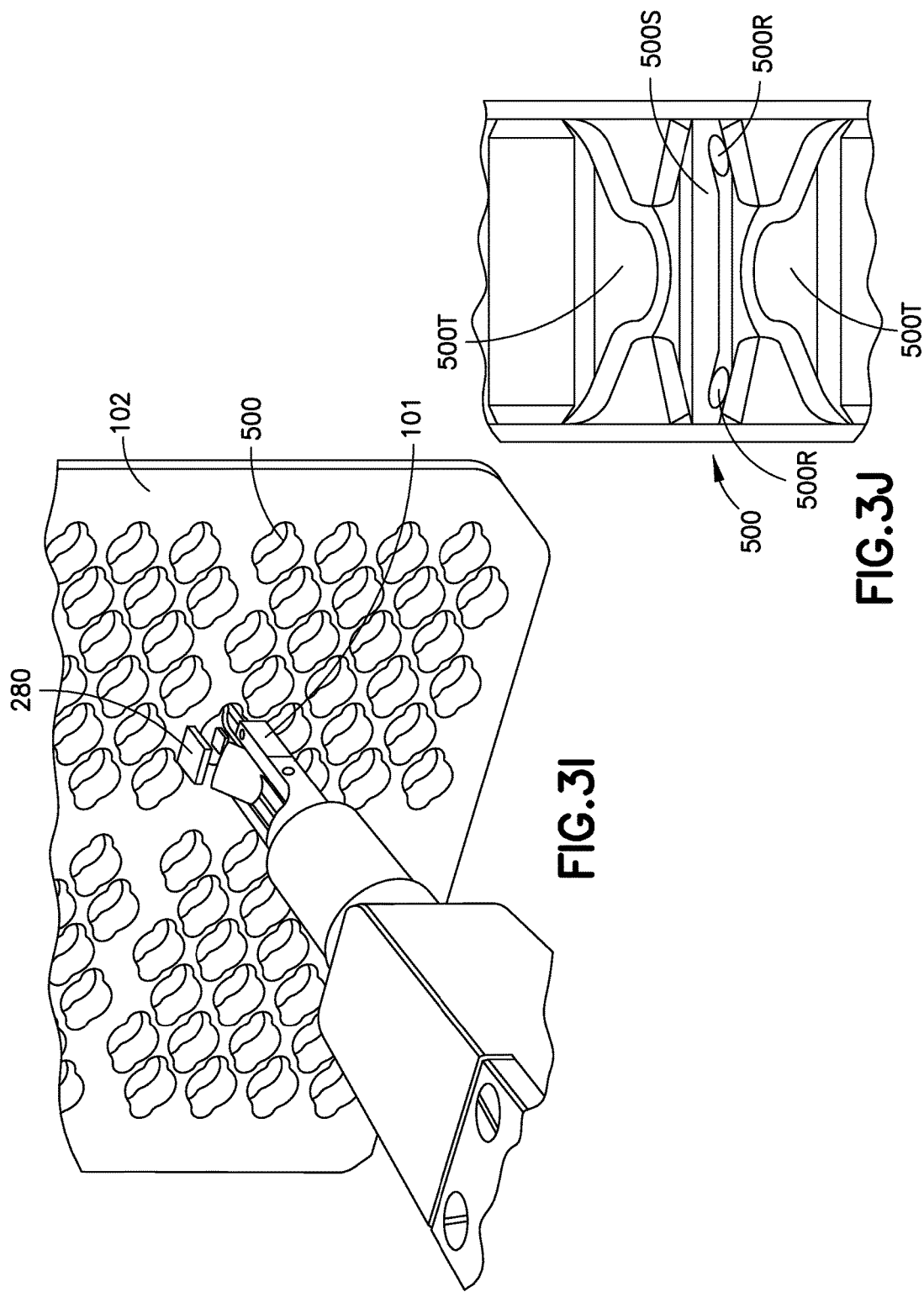

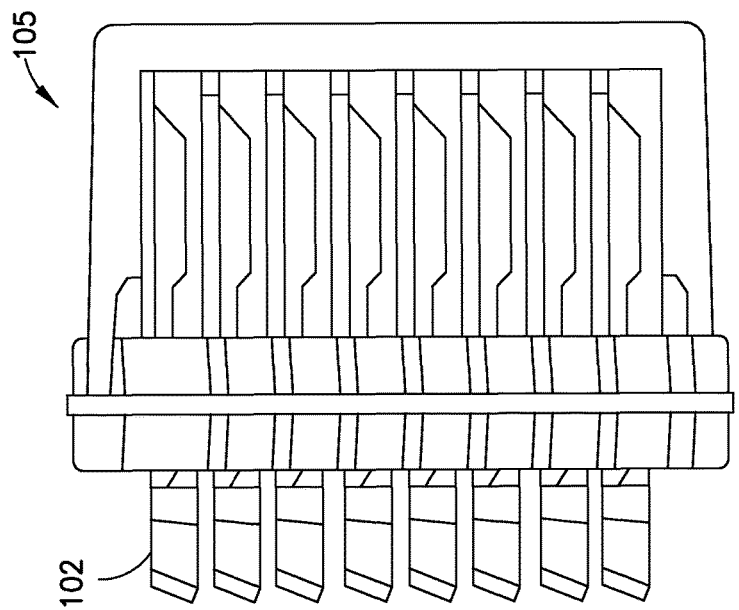
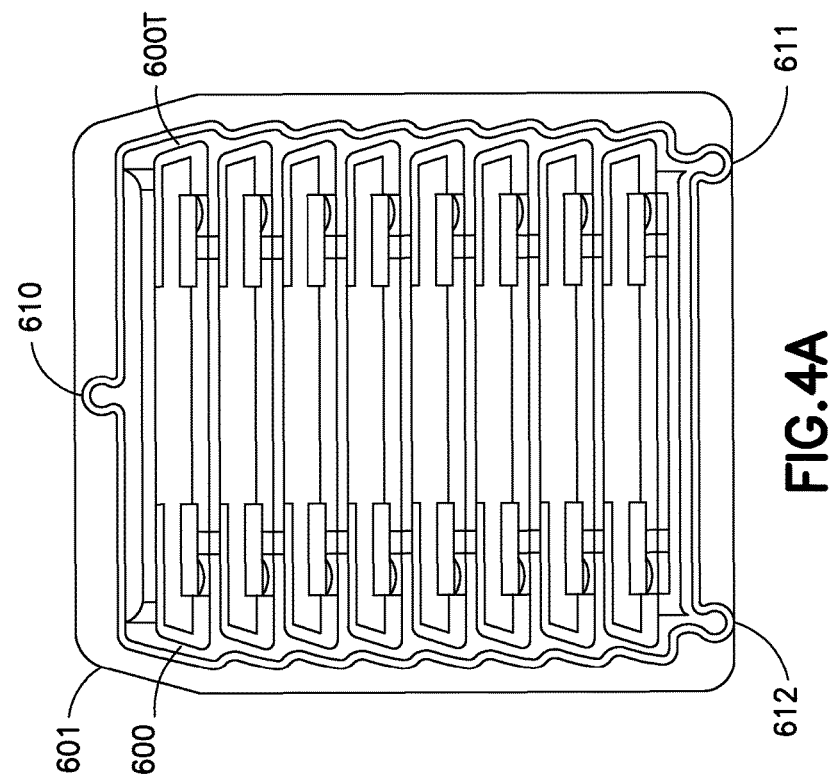
FIG.4B
FIG.4A

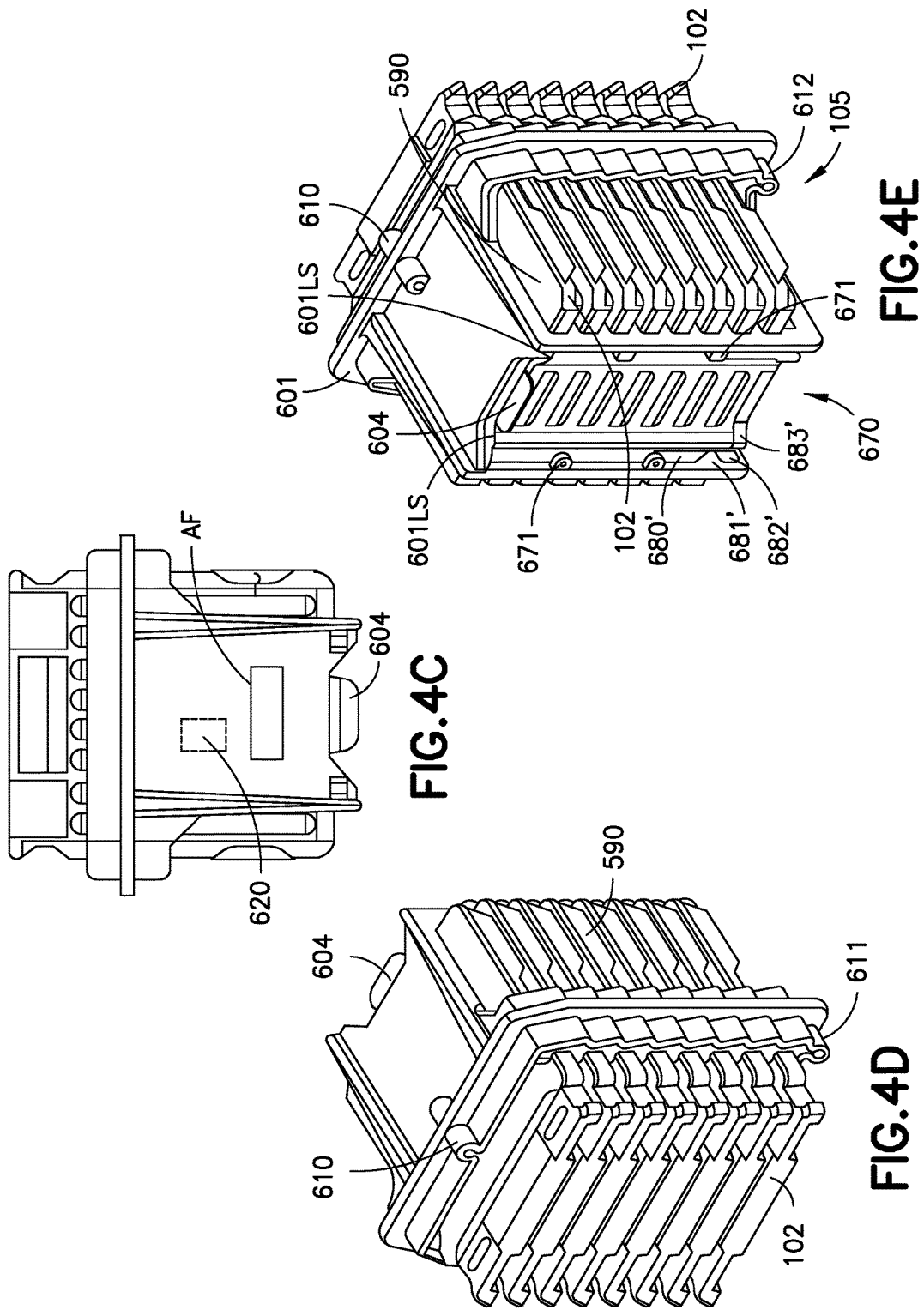

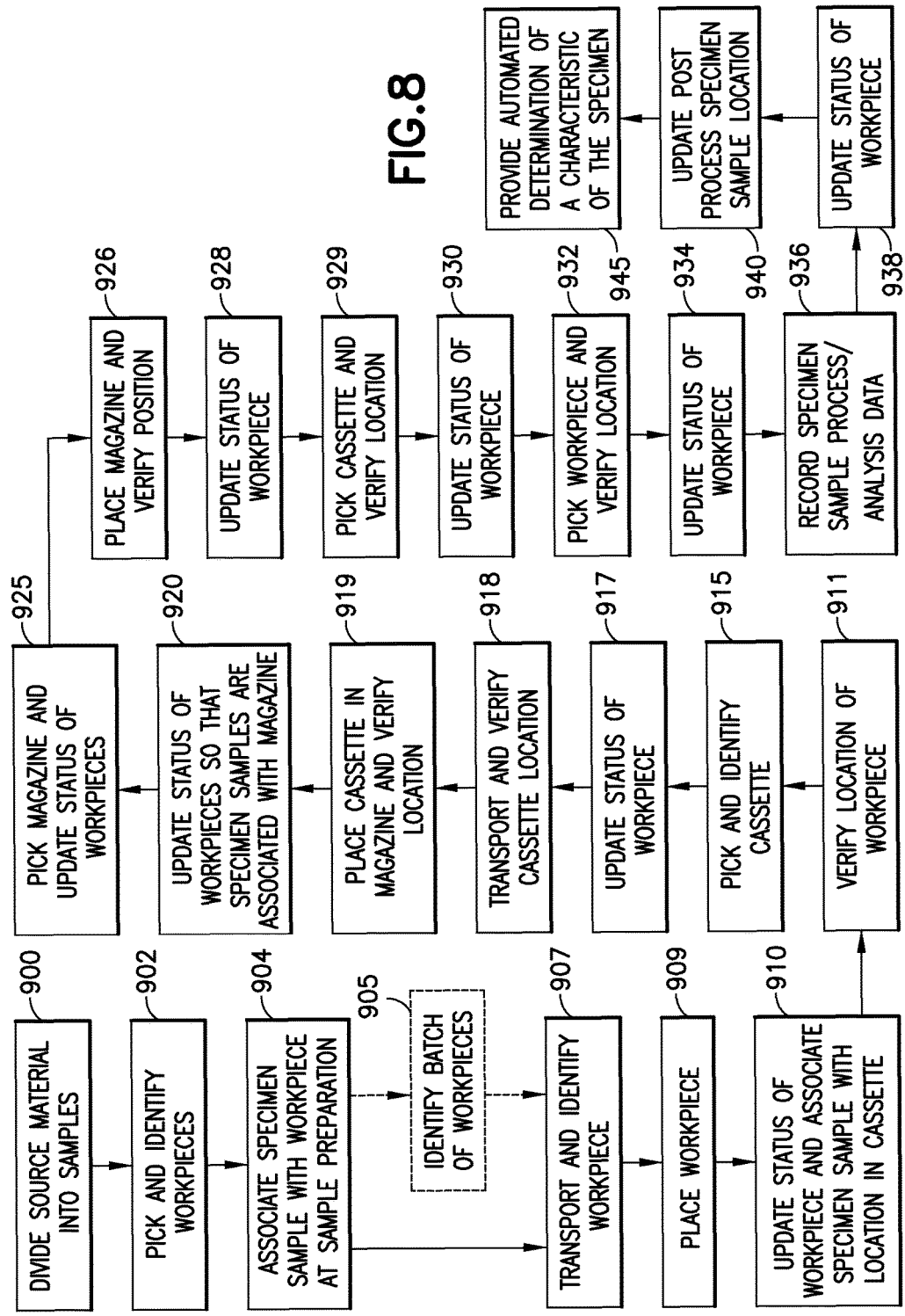

WORKPIECE HOLDER FOR WORKPIECE TRANSPORT APPARATUS

CROSS REFERENCE TO RELATED APPLICATIONS

This application is a non-provisional of and claims the benefit of U.S. provisional patent application No. 61/902,470 filed on Nov. 11, 2013 the disclosure of which is incorporated herein by reference in its entirety.

BACKGROUND

1. Field

The exemplary embodiments generally relate to automated workpiece processing systems and, more particularly, to automatic loading systems for automated processing systems.

2. Brief Description of Related Developments

Generally automated workpiece processing systems include workpiece transports and processing modules. The workpiece transports are generally employed to transport workpieces to and from the processing modules where the workpieces are placed on a workpiece holder for processing. During processing of the workpiece transports are removed from the process module and the process module is generally sealed.

Generally conventional workpieces are configured to hold samples/specimens. Conventional workpieces have simple identification markings, such as numbers however, these simple identification markings are limited in range and are not guaranteed to be a unique identifier. As such, tracking large numbers of samples held by conventional workpieces is difficult at best.

Generally workpieces are stored in workpiece holders. These workpiece holders are generally of low workpiece holding capacity and, with the exception of the largest cryogenic workpiece processing system, do not offer the capability to be automatically loaded into a workpiece processing system.

It would be advantageous to have a workpiece that is uniquely identifiable and able to be handled either manually or with automation. It would be advantageous to have a high capacity workpiece holding system that is capable of manual and/or automatic loading in a workpiece processing system that allows for batch processing of samples held by the workpieces as well as tracking of the samples.

In addition, conventional workpiece processing systems, such as electron beam imaging/scanning workstations do not have the ability to automatically track progress of a structure (which is divided into multiple specimens/samples) during processing of that structure.

It would be advantageous to be able to track and analyze multiple specimens during processing as a whole with respect to the structure being analyzed.

BRIEF DESCRIPTION OF THE DRAWINGS

The foregoing aspects and other features of the disclosed embodiment are explained in the following description, taken in connection with the accompanying drawings, wherein:

FIG. 1A is a schematic illustration of an automatic specimen/sample loading system in accordance with aspects of the disclosed embodiment;

FIGS. 2A-2D are schematic illustrations of a workpiece in accordance with aspects of the disclosed embodiment;

FIGS. 3A-3G, 3I and 3J are schematic illustrations of a specimen cassette in accordance with aspects of the disclosed embodiment;

FIGS. 4A-4F are schematic illustrations of a cassette magazine in accordance with aspects of the disclosed embodiment;

FIG. 8 is a flow diagram of an operation of the automatic specimen loading system of FIG. 1A in accordance with aspects of the disclosed embodiment.

DETAILED DESCRIPTION

Figure 1B:
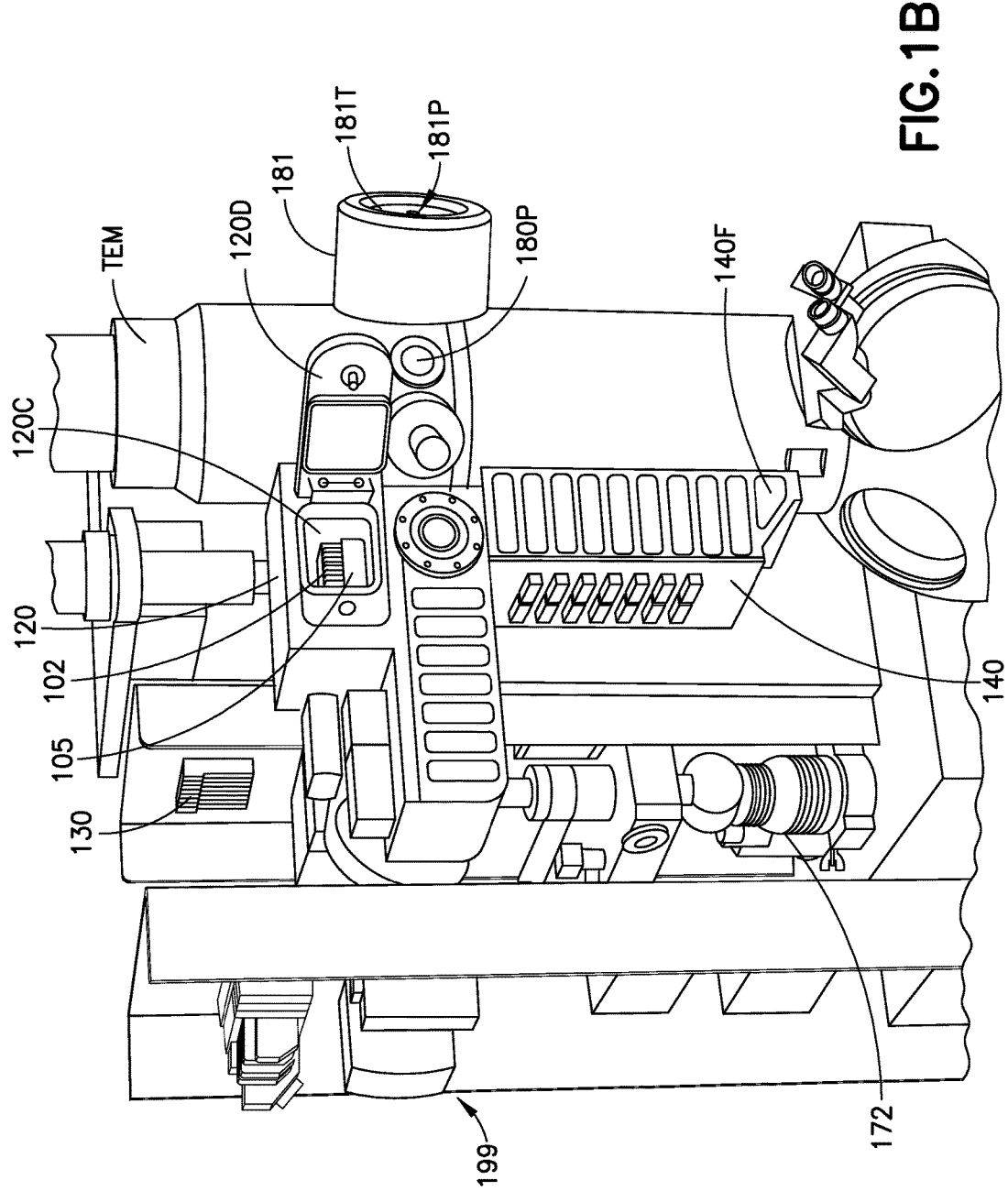
FIGS. 1B-1D are schematic illustrations of portions of the automatic specimen loading system of FIG. 1A in accordance with aspects of the disclosed embodiment.

FIG. 1 is a schematic illustration of an automated transport and positioning system 100 in accordance with aspects of the disclosed embodiment. Although the aspects of the disclosed embodiment will be described with reference to the drawings, it should be understood that the aspects of the disclosed embodiment can be embodied in many forms. In addition, any suitable size, shape or type of elements or materials could be used. It is also noted that while X, Y and Z axis are referred to, reference to these axes is exemplary only and in other aspects the axes have any suitable directional identifiers.

It should also be understood that while the aspects of the disclosed embodiments are described herein with respect to a transmission electron microscope (TEM), the aspects of the disclosed embodiment can be applied to any suitable workpiece processing equipment having a process module PM where a workpiece is supported on a stage or workpiece holder during processing of the workpiece. For example, aspects of the disclosed embodiment are employed in any suitable metrology equipment where a workpiece is held by the end effector of the disclosed embodiment during measurement/inspection or other processing. As will be described below, in one aspect, the stage is an end effector 101 of a workpiece positioning unit 104 of an automated transport and positioning system 100 while in other aspects the stage is an existing positioning stage PS of the process module PM.

In one aspect, in the context of the TEM, the automated transport and positioning system 100 provides loading and storage of about 500 to about 1000 specimens (also referred to herein as samples) in a single exchange (e.g. loading of specimens) while in other aspects related to the TEM or other suitable workpiece processing equipment (such as those mentioned above) more or less workpieces are loaded and stored. In one aspect, the automated transport and positioning system 100 replaces the conventional positioning "stage" PS used in, for example, TEMs that positions specimen holders or grids within the TEM during imaging. In other aspects the automated transport and positioning system 100 replaces any suitable loading system of, for example, any suitable metrology or other processing equipment. In one aspect, the automated transport and positioning system 100 also provides for complete, high-resolution, high-speed, high-stability position control of the workpiece during imaging or inspection. As will be described below, in accordance with the aspects of the disclosed embodiment, the grid handling and storage operations as well as the positioning of the specimen in the TEM column is effected with, in one aspect, eight controlled degrees of freedom and, in other aspects, with nine controlled degrees of freedom.

As will also be described below, the automated transport and positioning system 100 includes a loading unit 140 that has an end effector 101 configured to substantially directly handle any suitable workpiece such as a grid (or other suitable specimen holder) with or without, for example, the use of a carrier or adapter that interfaces the workpiece with the handling system. In one aspect a gripper of the end effector 101 is operated through coordinated movement of two or more of the, in one aspect, eight controlled degrees of freedom and, in other aspects, nine controlled degrees of freedom, which when combined act to open and close the gripper while maintaining the end effector position constant relative to the workpiece. In other aspects the gripper of the end effector is operated in any suitable manner such as with a dedicated drive that drives the gripper. In one aspect, the end effector 101 is configured to manipulate the workpiece in a high vacuum environment or any other suitable environment such as a non-vacuum or low vacuum environment. The end effector 101 is configured to grip individual workpieces during extraction from any suitable workpiece holding cassette 102 as well as be configured for the placement and removal of the workpieces to and from a pre-aligner stage 103 for rotational alignment of the workpiece. In one aspect the end effector 101 (and the workpiece positioning unit or multistage shuttle 104 which the end effector is a part of) is configured to provide a precision and rigid interface to support the grid mounted specimen which enables fast position moves (e.g. about 8 to about 24 microns or any other suitable distance) and rapid settling (e.g. to about less than 5 nanometers) in less than about 100 ms substantially without introducing undesired vibrational modes in the workpiece during imaging. In other aspects the end effector 101 (and the workpiece positioning unit 104 which the end effector is a part of) is configured to perform fast position moves (e.g. about 8 to about 24 microns or any other suitable distance) and rapid settling (e.g. to about less than 4 nanometers) in less than about 25 ms to about 35 ms substantially without introducing undesired vibrational modes in the workpiece during imaging. It is noted that while the end effector 101 is shown has having a single workpiece holding gripper in other aspects the end effector is configured to hold multiple workpieces in, for example, a side by side arrangement or any other suitable arrangement. The end effector 101 and the workpiece positioning unit 104 are substantially similar to that described in U.S. Provisional Patent application No. 61/902,470 filed on Nov. 11, 2013 and U.S. patent application Ser. No. 14/538,391 entitled "Workpiece Transport and Positioning Apparatus" and filed on Nov. 11, 2014, the disclosures of which are incorporated herein by reference in their entireties. In one aspect (as also described in for example U.S. patent application Ser. No. 14/538,391 entitled "Workpiece Transport and Positioning Apparatus" and filed on Nov. 11, 2014, the disclosure of which was previously incorporated herein by reference in its entirety), the automated transport and positioning system 100 includes a drive section having multiple degrees of freedom (in one aspect at least three degrees of freedom) for effecting any suitable processing of samples within the process module including but not limited to thin section tomography.

As will be described below, in one aspect, handling (e.g. picking and placing) of the workpiece is performed utilizing a vision system or other suitable optical and/or radio frequency reader that includes one or more cameras or optical detectors and/or an illumination unit integrated substantially directly into the end effector 101 and/or at other suitable locations off of the end effector where workpieces are imaged as described in, for example, U.S. Provisional Patent application No. 61/902,470 filed on Nov. 11, 2013 and U.S. patent application Ser. No. 14/538,391 entitled "Workpiece Transport and Positioning Apparatus" and filed on Nov. 11, 2014, the disclosures of which were previously incorporated herein by reference in their entireties. The integral vision system or other suitable optical and/or radio frequency reader provides substantially continuous monitoring of the workpiece handling operations and permits a closed loop control of each operation through any suitable image analysis algorithms that are stored in any suitable memory 199M of any suitable controller 199 connected to the automated transport and positioning system 100. In one aspect the controller is located remotely from the automated transport and positioning system 100 while in other aspects the controller is integrated with the automated transport and positioning system. It is noted that the controller 199 is suitably configured to control the automated transport and positioning system in the manner described herein. In one aspect the controller 199 is connected to, in any suitable manner, or integrated in a laboratory information management system LIMS for tracking the location of specimen samples within a laboratory or other facility as described herein. The vision system provides for workpiece fiducial (or other suitable features of the grid) detection to effect workpiece alignment during the workpiece handling operations. In other aspects the vision system provides for workpiece identification and/or effect controlled guided movement of the end effector.

In one aspect the workpieces or grids 400 are held in a batch holder such as in cassettes 102 where the cassettes 102 are held in batch holders such as one or more magazines 105 that are configured for insertion into the automated transport and positioning system 100 as will be described below. The magazine 105 and cassettes 102 therein are configured to provide for the automatic loading and removal of the cassettes 102 (and one or more workpieces/specimens, e.g. batches of workpieces/specimens, located therein). For example, the magazine 105 and cassettes 102 include kinematic features that permit substantially direct handling of the magazine 105 and cassettes 102 (e.g. as a unit or individually) by an automated handling system within the automated transport and positioning system 100 and external to the automated transport and positioning system 100. In one aspect the magazine 105 and cassettes 102 are configured for use in vacuum environments while in other aspects the magazine 105 and cassettes 102 are configured for use in non-vacuum environments.

Figure 1C:
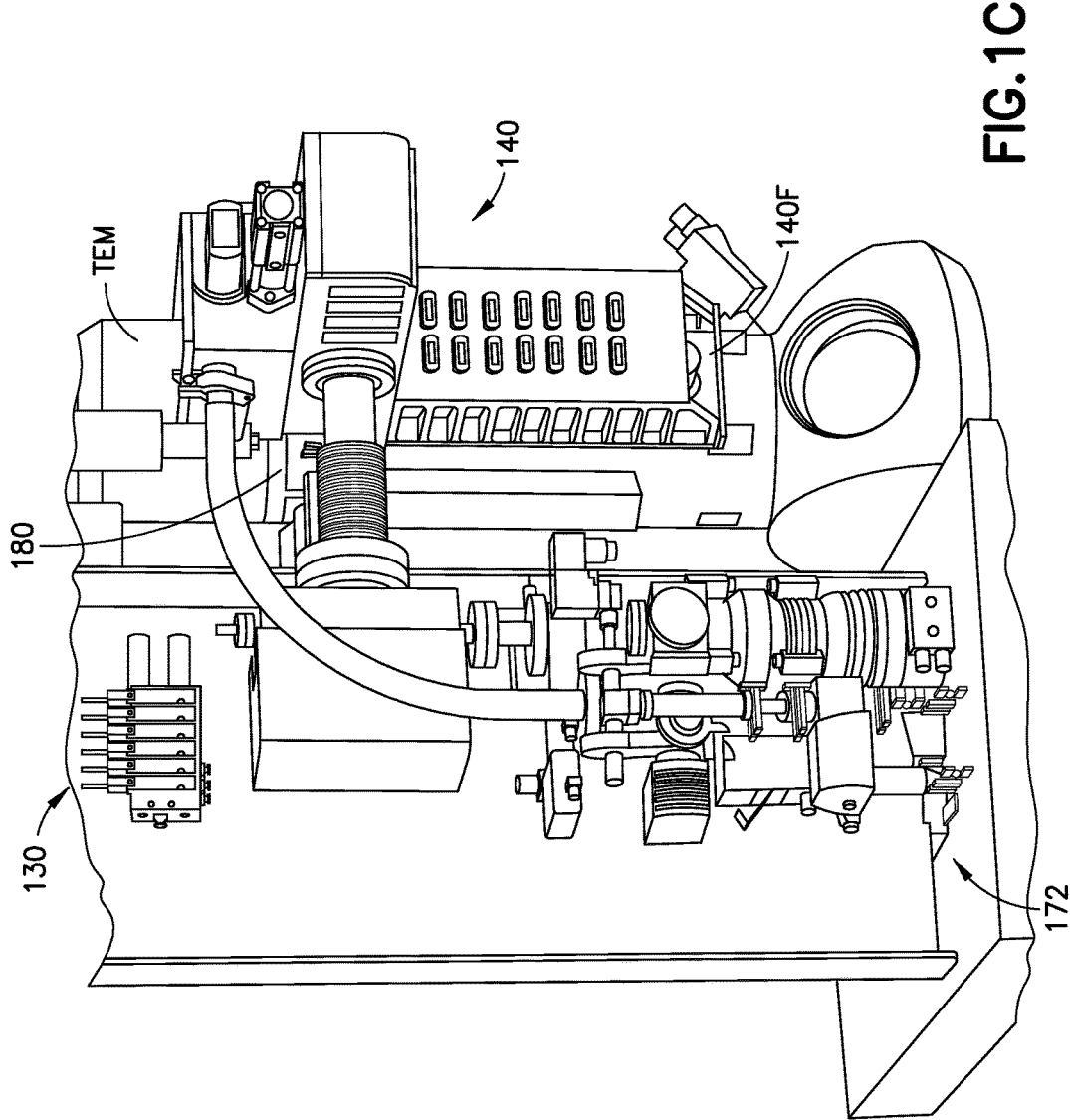
Figure 1D:
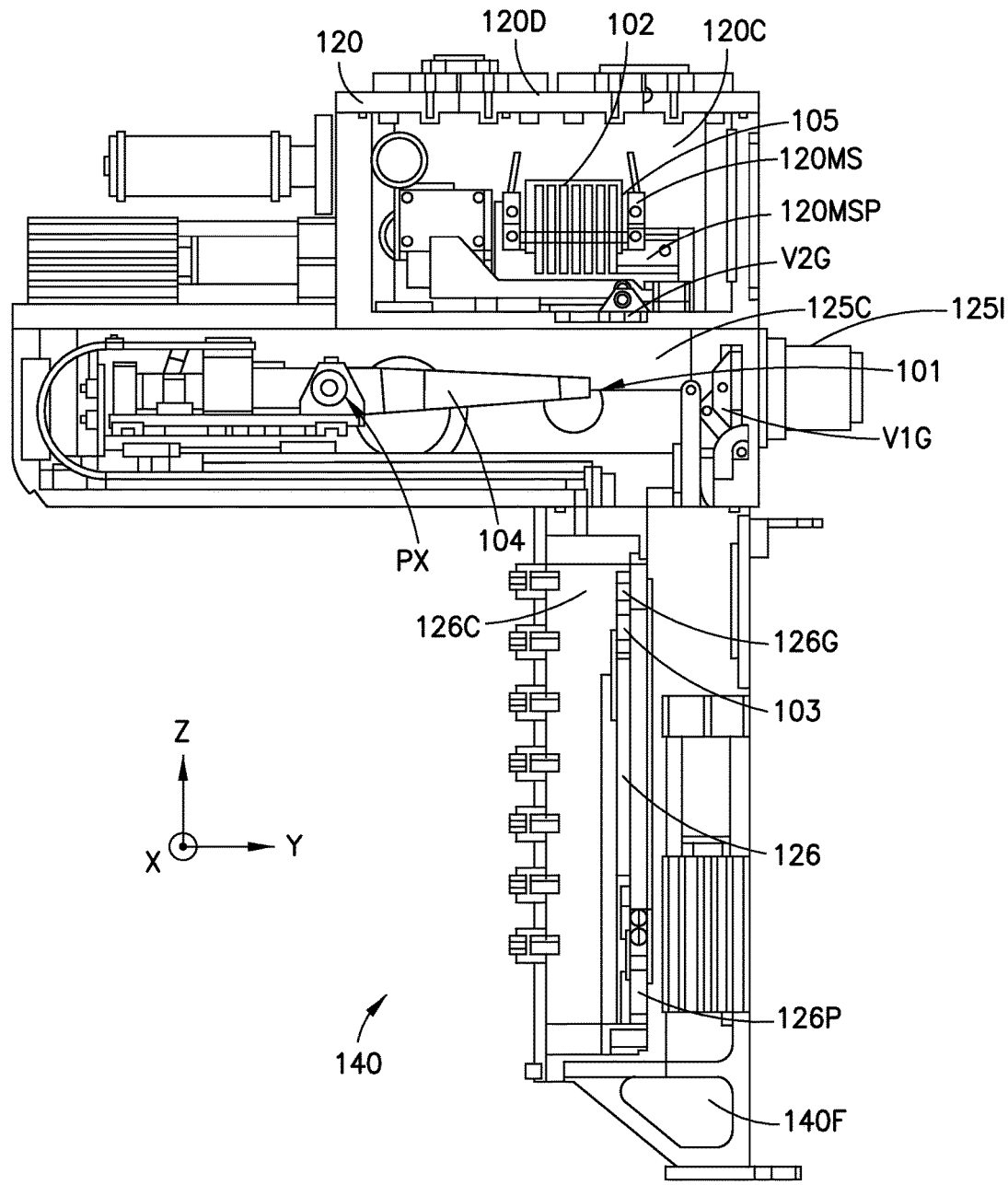

Still referring to FIG. 1A and also to FIGS. 1B-1D the automated transport and positioning system 100 includes a frame 140F, loading unit 140 connected to the frame 140F, a pneumatics module 130 (which may be connected to the frame and) communicably coupled to the loading unit 140, and a vacuum module 172 (which may be connected to the frame) and communicably coupled to the loading unit 140. In one aspect the pneumatics module 130 includes an air source 130S and any suitable valves V1G, V2G, V3T, V4R, V5R, V6 for operating, e.g., valves and closures of the loading unit 140 and/or vacuum module 172 described herein. The vacuum module 172 includes any suitable vacuum pumps P1R, P2T, P3I and gauges G1R, G2H, G3H, G4H for pumping and maintaining the internal chambers of the loading unit 140 at any suitable vacuum pressure for interfacing with, for example, the TEM or other suitable process module PM. In one aspect the vacuum module 172 also includes any suitable valves V3T, V4R, V5R, V6, V7T, V8V, V9V for selectively isolating, e.g., the vacuum pumps from each other and/or from the chambers of the loading unit 140.

In one aspect the frame 140F forms or is integral (e.g. of one piece unitary construction) to at least part of the loading unit 140. In other aspects the loading unit 140 is connected to the frame 140F in any suitable manner. In one aspect the loading unit 140 includes an automated loading and transport section or load lock 120 having a sealable chamber 120C and a transport module or section 125 having a sealable chamber 125C. The chamber 120C is selectively communicably connected to the chamber 125C through a closable opening or port 120P. In one aspect the loading unit 140 includes any suitable gate valve V2G configured to selectively seal the port 120P for sealing or otherwise isolating an atmosphere of the chamber 120C from an atmosphere of the chamber 125C. The load lock 120 includes any suitable door 120D configured to seal a loading opening of the load lock 120. While a single door 120D is illustrated in the figures as being located on a side of the chamber 120C it should be understood, in other aspects, the single door 120D is located on a top of the chamber 125C (see FIG. 1D—e.g. to allow for automated opening and closing of the door for overhead loading of magazines 105 in the chamber) or in still other aspects more than one door (e.g. on a top and on a side) provides access to the chamber 125. In one aspect the door is hinged to the load lock 120 while in other aspects the door is removable from the load lock 120D for allowing access to the chamber 120C. In one aspect the door 120D has a manual closure, and in other aspects the door 120D has an automated closure. In other aspects the chamber 120C may not include a door such that the atmosphere within chamber 125C is cycled between, for example, a process atmosphere and atmospheric pressure when cassettes are introduced and removed to and from the chamber 125C. The loading opening is configured to allow ingress and egress of one or more workpieces to and from the chamber 120C. In one aspect, as will be described further below, the workpieces are TEM grids held by cassettes 102 which in turn are held in a magazine 105. In one aspect the load lock includes an automated transport shuttle 120MS including a positioner unit 120MSP. The positioner unit 120MSP includes any suitable motors and/or guides for allowing movement of the transport shuttle 120MS within the chamber 120C and be configured for operation in one or more of a vacuum or atmospheric environment. The positioner unit 120MSP includes any suitable drive or motor A1L for moving the transport shuttle 120MS along at least the Y axis. In one aspect the motor A1L is a DC stepper motor that drives a screw drive for positioning the transport shuttle 120MS with a positioning resolution of about 5um. In other aspects the motor is any suitable motor having any suitable positioning resolution such as a piezo motor, brushless or brushed motors, etc. The transport shuttle 120MS is configured to hold one or more magazines 105 and transport or otherwise move the magazines (e.g. via the positioner unit 120MSP) in one or more of the X and Y directions so that a predetermined cassette 102 is aligned with the port 120P for transport into the chamber 125C as will be described below. The transport shuttle 120MS includes any suitable kinematic features that mate with corresponding kinematic features (described below) of the magazine 105 for positioning the magazine relative to the transport shuttle 120MS. As may be realized, in one aspect, the kinematic features are also configured so that the magazine 105 can be placed on the transport shuttle 120MS in only one predetermined orientation. In other aspects, the transport shuttle 120MS includes any suitable features for positioning the magazine 105 on the transport shuttle 120MS in any suitable number of orientations and in any suitable manner. In one aspect the magazines 105 and the load lock 120 are configured for manual operator insertion and removal of the magazine 105 to and from the load lock 120 while in other aspects the magazines 105 and the load lock 120 are configured for automated insertion and removal of the magazine 105 to and from the load lock 120.

In one aspect the transport module 125 includes a process module interface 125I configured to couple and uncouple the loading unit 140 to and from a corresponding interface, such as interface or port 180P, of the process module PM so that the loading unit can be installed to or removed from the process module PM as a unit. The process module interface 125I includes a closable opening or port 125P that communicably connects the chamber 125C with an interior of the process module PM. The loading unit 140 includes any suitable gate valve V1G configured to selectively seal the port 125P for sealing or otherwise isolating an atmosphere of the chamber 125C from an internal atmosphere of the process module PM.

In one aspect the transport module 125 includes a cassette shuttle chamber 126C communicably connected to the chamber 125C. The cassette shuttle chamber 126C includes a workpiece or cassette shuttle 126 that is driven along any suitable axes by a workpiece shuttle positioner 126P. The workpiece shuttle positioner 126P includes any suitable drives or motors A2L and/or guides for allowing movement of a cassette shuttle gripper 126G along at least the Z axis. In one aspect the motor A2L is an ultrasonic piezo motor with less than about 1 um positioning resolution while in other aspects the motor A2L is any suitable motor having any suitable position resolution such as stepper motors, brushless motors, brushed motors, etc. The cassette shuttle gripper 126G is opened and closed in any suitable manner by any suitable drive A9R (e.g. such as by a two-state or open/closed actuator). In one aspect the workpiece shuttle 126 is a linear stage configured to move (via the workpiece shuttle positioner 126P) a cassette gripper 126G mounted to the workpiece shuttle 126 into a position (e.g. through the port 120P) for picking/removing and placing/inserting a cassette 102 from and to a magazine 105 located in the chamber 120C. The workpiece shuttle 126 is also configured to move the cassette 102, held by the cassette gripper 126G, to a predetermined pick/place position or workpiece holding station 176 along at least the Z axis to allow the end effector 101 of the workpiece positioning unit 104 to remove and/or insert a workpiece from and/or to the cassette 102. In one aspect the workpiece shuttle 126 is also configured to move the cassette 102, held by the cassette gripper 126G, to a predetermined buffer position (as will be described below) to allow the workpiece positioning unit 104 to move along at least the Y axis for transporting the workpiece to the processing module PM for processing without returning the cassette 102 to the magazine 105.

In one aspect a workpiece pre-aligner stage 103 is mounted to the cassette shuttle 126 (e.g. the pre-aligner stage and the cassette shuttle 126 move along at least the Z axis as a unitary member) for aligning workpiece prior to or post processing of the workpieces in the processing module PM. In other aspects the pre-aligner stage 103 is mounted to the frame 140F independent of the cassette shuttle 126 so that the pre-aligner stage is stationary along the Z axis or is movable along the Z axis independent of the cassette shuttle 126. The pre-aligner stage 103 includes any suitable drive A8R configured to provide rotation of the workpiece about the Z axis. In one aspect the drive A8R includes a brushless DC motor, an 800:1 gearbox (or any other suitable gearbox having any suitable drive ratio) and an encoder providing about 0.03 degree resolution. In other aspects the drive A8R is any suitable motor having any suitable gearbox and encoder providing any suitable degree of resolution. In operation, as will be described below the workpiece positioning unit 104 picks a workpiece 400 (see e.g. FIG. 2A for exemplary purposes only) from a cassette 102 and transports the workpiece to a rotational chuck of the pre-aligner stage 103 for workpiece orientation.

Referring now to FIGS. 2A-2D the workpiece 400 is illustrated. In one aspect the workpiece is substantially similar to that described in U.S. Provisional Patent application No. 61/902,470 filed on Nov. 11, 2013 and U.S. patent application Ser. No. 14/538,332 entitled "Specimen Sample Holder for Workpiece Transport Apparatus" and filed on Nov. 11, 2014, the disclosures of which are incorporated herein by reference in their entireties. The workpiece 400 is any suitable workpiece and is illustrated as a TEM grid specimen holder for exemplary purposes only. In one aspect the workpiece 400 has a disc configuration but in other aspects the workpiece has any other suitable shape. In one aspect, the workpieces 400 have a half-moon shape (e.g. a lift out workpiece/grid) as described in U.S. patent application Ser. No. 14/538,332 entitled "Specimen Sample Holder for Workpiece Transport Apparatus" and filed on Nov. 11, 2014, the disclosure of which was previously incorporated herein by reference in its entirety. The workpiece 400 includes a thin sheet base member BM with a first surface 400T and an opposing second surface 400B, the first surface defining a seat and support surface for a specimen holding film held by the workpiece 400. In one aspect the base member BM is constructed of a beryllium copper alloy while in other aspects the base member is constructed of any suitable material. In still other aspects the base member BM is a sub-millimeter thick sheet while in other aspects the base member BM has any suitable thickness.

The base member BM includes an aperture or slot 401 (which will be described in greater detail below) through the second surface 400B exposing the holding film held by the sample/specimen holder, and including a grip engagement zone GZ defined at least on part of the first surface 400T and arranged to accept engagement of the gripper of the end effector 101, 301. In one aspect the grip engagement zone GZ of the base member BM for the gripper is a 360 degree radial area adjacent or at a peripheral edge of the base member BM. In other aspects, the base member BM includes a recess 400R on, for example, the second surface 400B (e.g. opposite surface 400T) to provide a gripping surface so that the workpiece 400 is gripped manually, with automation, or in any other suitable manner. As will be described in greater detail below at least one of the first or second surface 400T, 400B includes machine readable structures formed thereon arranged in patterns embodying data that is a physical representation of a specimen or sample held on a respective workpiece where the physical representation of the specimen or sample, in one aspect, defines at least one predetermined characteristic of the sample holder as will be described in greater detail below. As will also be described below, the predetermined characteristic may be a unique identification indicia of the sample and/or sample holder, with error correction characteristics.

As described above, the workpiece 400 includes a slot 401 in which a specimen is held. In one aspect the slot 401 has any suitable predetermined length L and any suitable width W1, W2, W3 (while three widths are illustrated in other aspects the workpiece 400 may be provided with a slot having any suitable width and/or length or an aperture having any suitable geometrical shape). In this aspect the slot is an open slot but in other aspects the slot may include any suitable mesh or other suitable geometry for holding one or more specimens. In still other aspects the workpiece may not include a slot. In one aspect the corner of the slot 401C is rounded to, for example, provide more imagable area to rectangular specimen samples.

In one aspect, as noted above, the workpiece 400 includes one or more suitable structures or identifying indicia (e.g. readable data storage medium) that define three dimensional topography with respect to a reference plane of the at least one first or second surface 400T, 400B on which the structures are disposed and wherein the structures are formed integral with the at least one first or second surface 400T, 400B on which the structures are disposed. In one aspect the structures are disposed symmetrically on at least the first or second surface 400T, 400B providing redundant reading locations while in other aspects the structures have any suitable arrangement relative to each other and/or the first or second surface 400T, 400B. In one aspect the structures are identifiers, such as two dimensional datamatrix barcodes 402A, 402B that may be formed on a first surface 400T (e.g. from which the specimens are viewed) of the workpiece 400 in any suitable manner and at any suitable locations. In one aspect the barcodes 402A, 402B are engraved or micro-machined on the surface on opposite sides of the slot 401. In one aspect each barcode may be a one dimensional or two dimensional barcode that includes at least 14 cells along a length of the barcode (e.g. for 1-D a barcode) or at least one side of the barcode (e.g. for a 2-D barcode). In other aspects more or less than 14 cells are provided along the length of the barcode. For example, in one aspect, the barcode may be a 14×14 datamatrix that has the capacity to encode $3.6 \times 10^{15}$ unique 10-character alphanumeric serial numbers (which, in one aspect, are used in a manner similar to and/or embody accession numbering where the accession numbering corresponds to specimen samples that are registered in, for example, data structure DS and/or the laboratory information management system LIMS such that the accession numbering defines an ordered sequence of the workpieces 400 holding the specimen samples) with error correction to uniquely identify a specimen as described herein in for example the laboratory information management system LIMS or other any suitable database or tracking system. In other aspects the barcodes 402A, 402B have any suitable size and are configured to provide any suitable serial numbers or other information such as alphanumeric serial numbers having more or less than 10 characters. In one aspect the barcodes 402A, 402B are used in conjunction with other identifiers on, for example, the cassettes 102 and/or magazines 105, to identify which magazine and/or cassette the sample is located. Multiple barcodes 402A, 402B are provided to provide redundancy in the event one barcode is obscured or damaged and allow the barcodes to be read from many viewing angles. The structures also define a human readable identifier 403 on the first or second surface 400T, 400B to allow an operator to manually read the identifier 403 and to identify (e.g. without a barcode reader) the specimen(s) located on the workpiece 400. In one aspect the identifier 403 may be a 10-character alphanumeric serial number (e.g. that matches or otherwise corresponds to the serial number(s) of the barcode). In one aspect the identifiers 402A, 402B, 403 are unique and different than identifiers of, for example, the cassettes 102 and magazines 105 described herein. In one aspect the identifiers 402A, 402B, 403 are related to a predetermined sequence of specimens (e.g. as will be described below) in an array of workpieces 400; correspond to a predetermined arrangement of an array of workpieces 400 in the pockets 500 of a cassette 102 (described in greater detail below); are representative of a source material configuration from which the specimens on the workpieces 400 are made (as will be described in greater detail below); and/or comprises workpiece 400 identification data relating each workpiece, in an array of workpieces in the pockets 500 of a cassette 102, and a specimen disposed on the workpiece 400. In one aspect, the workpiece identifiers 402A, 402B and 403 are in the form of an active or passive electronic chip such as an RFID chip, Bluetooth transmitter or other suitable wireless identifier configured to be read by any suitable scanner SCR disposed within, for example, the automated transport and positioning system 100 and/or within any suitable portions of the workpiece processing system or facility 100PS (described in greater detail below, see FIGS. 7 and 7A).

In one aspect the structures define one or more machine readable fiducial 404A-404D relating a specimen position to end effector gripper or holder position. In one aspect the at least one fiducial 404A-404D includes more than one unique fiducial, each of which independently identifies the relative position of the specimen to the holder. The fiducials 404A-404D are also provided in any suitable manner, such as by etching, engraving or micro-machining, on the first surface 400T. These fiducials 404A-404D provide an absolute physical reference between the specimen mounted to the workpiece and the workpiece physical boundaries (e.g. the edges of the slot 401 and/or the peripheral edge of the workpiece). In one aspect the workpiece detecting member 280 (along with any suitable image processing performed by, for example, controller 199) is configured to read or otherwise detect the fiducials 404A-404D for aligning the end effector with the workpiece for picking the workpiece, aligning the workpiece held by the end effector 101 with a workpiece holding station for placing the workpiece, for rotating the workpiece during alignment on the pre-aligner stage 103, for aligning the workpiece with a beam of the TEM and/or for any other suitable purpose. As may be realized the barcodes and fiducials provide for automated, high-throughput machine-based recognition and handling of the workpieces for substantially unassisted specimen loading, positioning, verification, quality control, and handling for high-throughput and controlled environment applications.

In one aspect the structures provide tailored optical properties of the first and/or second surface 400T, 400B. For example, in one aspect, the structures define retro-reflection features providing a predetermined optical response. In one aspect any suitable number (such as, e.g., hundreds, and even thousands) of miniature tuned "corner cube" and/or "cat's eye" retroflecting features are be etched, engraved or otherwise micro-machined into the surface of the workpiece 400 to provide optimal optical response (contrast, and possibly even wavelength filtering) at the macro level.

As may also be realized, the slot 401 is suitably positioned away from the gripping zone GZ and/or recess 400R so that the gripper of the end effector 101, 301 does not contact or obstruct the specimen. It is noted that, in one aspect, the workpiece 400 may not include the recess in the gripping zone GZ of the workpiece 400. It is noted that the slot 401 has any suitable orientation relative to the recess 400R/gripping zone GZ as illustrated in FIGS. 2C and 2D.

Referring to FIGS. 3A-3I the cassette 102 is illustrated in accordance with aspects of the disclosed embodiment. In this aspect the cassette 102 is illustrated as having a rectangular shape cassette frame 102F but in other aspects the cassette 102/cassette frame 102F has any other suitable shape and/or configuration. The cassette frame 102F includes one or more workpiece 400 holding stations or pockets 500 arranged in a grid such that the pockets are accessible from a first side 102T of the cassette 102. In this aspect the grid includes and 8×8 array of pockets 500 for holding 64 individual workpieces 400 but in other aspects the grid has any suitable number of columns and rows such as for example, an 8×16 array for holding 128 individual workpieces. In one aspect the cassette also includes column and row identifiers (e.g. such as alphanumeric characters, barcodes, etc.) on the first side 102T (or at any other suitable location) for allowing operator and/or machine identification of a location of each pocket 500. For example, the columns are identified by a sequential series of numbers 1-8 and the rows are identified by a sequential series of letters A-H (or vice versa) however, in other aspects any suitable identifiers may be used. The cassette 102 also includes any suitable machine readable and/or human readable indicia for identifying the cassette. For example, the cassette has a longitudinal axis LA1 and a lateral axis LA2 so as to define lateral sides SL1, SL2 and longitudinal sides SL3, SL4. In one aspect the first side 102T (from which the workpieces are accessed) includes readable data storage media such as any suitable number of barcodes 501A and human readable indicia 502A (such as serial numbers) which, in one aspect, is substantially similar to those described above with respect to workpiece 400. As may be realized, in one aspect, other surfaces such as longitudinal surface or side SL4 also include similar barcodes 502B and human readable indicia 502B so that the cassette 102 is identified or identifiable while located within, for example a magazine 105. As may be realized, the barcodes 501A and human readable indicia 502A comprise cassette identification data that relates the cassette and an array of workpieces 400 held on the cassette to a source material configuration (the source material configuration being described in greater detail herein, see e.g. FIG. 7B). In one aspect, the cassette identifiers 501A, 502A are in the form of an active or passive electronic chip such as an RFID chip, Bluetooth transmitter or other suitable wireless identifier configured to be read by any suitable scanner SCR disposed within, for example, the automated transport and positioning system 100 and/or within any suitable portions of the workpiece processing system or facility 100PS (described in greater detail below, see FIGS. 7 and 7A).

Figure 7:
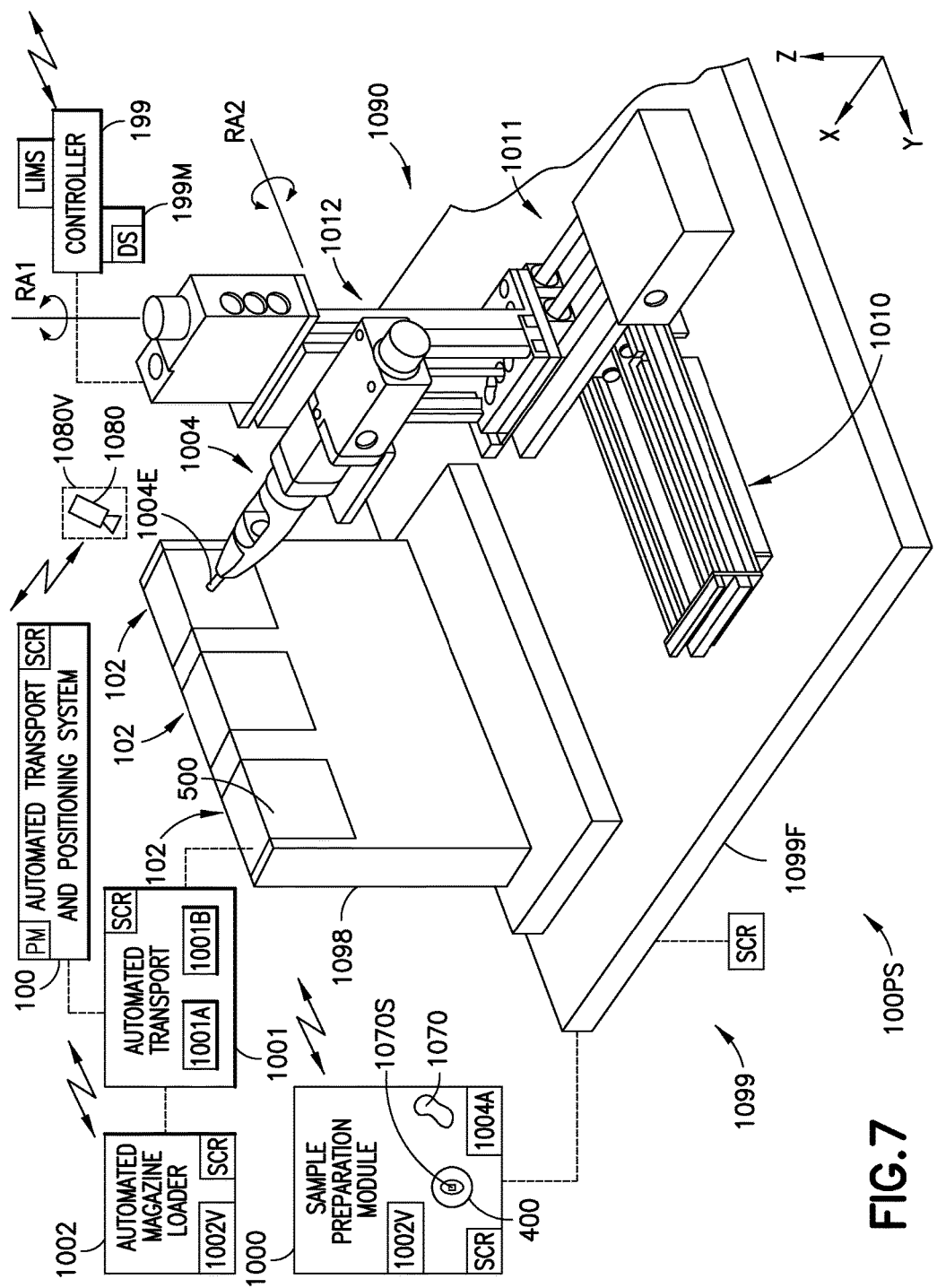
FIGS. 7 and 7A are schematic illustrations of a processing system in accordance with aspects of the disclosed embodiment.
Figure 7A:
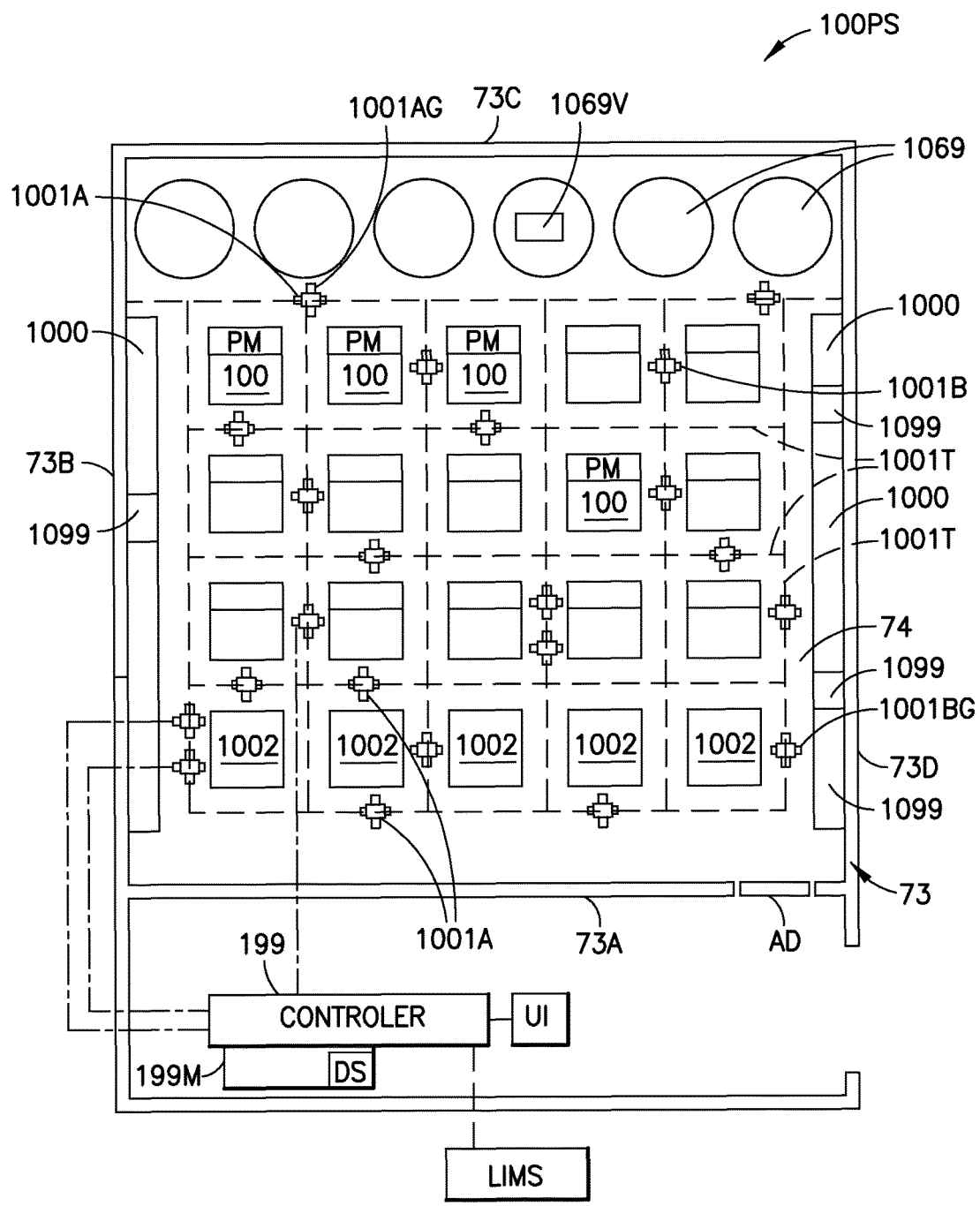
Figure 7B:
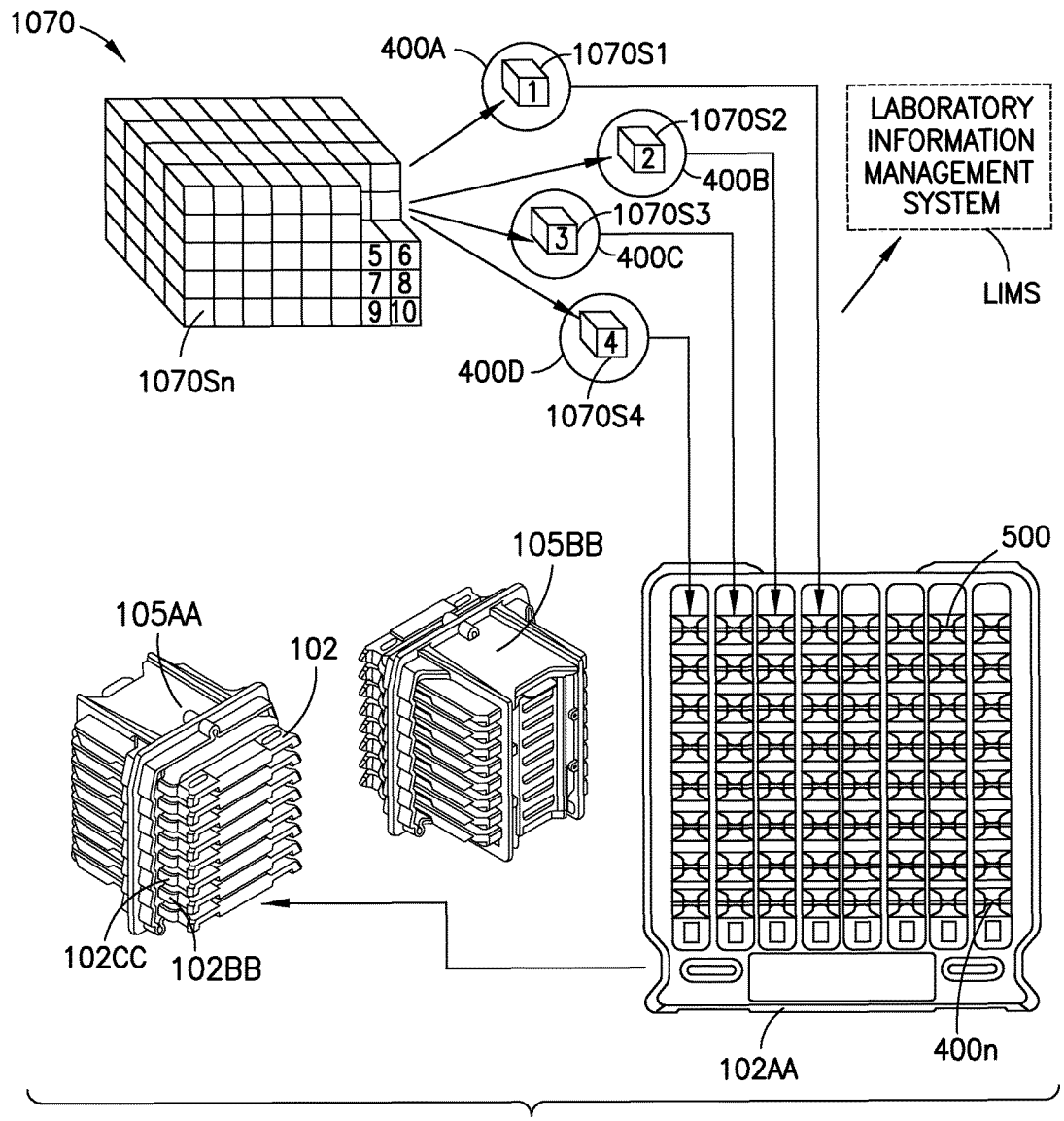
FIG. 7B is a schematic illustration of a portion of a process of the processing system in accordance with aspects of the disclosed embodiment.

As may be realized referring to FIG. 7B, in one aspect, workpieces 400A-400*n* are arranged or otherwise placed within respective pockets 500 of a cassette 102AA in a predetermined ordered sequence, where the ordered sequence corresponds to, for example, one or more of a predetermined arrangement of an array of workpieces 400 in the array of pockets 500, a structure STR of a specimen/ structure 1070 the samples 1070S1-1070Sn on the workpieces were taken from or any other suitable criteria. In one aspect, the predetermined ordered sequence of workpieces (and hence a predetermined ordered sequence of specimens located on the workpieces) is defined coincident with loading of each workpiece in an array of workpieces in a cassette 120 as described herein. As can be seen in FIG. 7B, the structure or specimen 1070 is divided into samples 1070A-1070*n* where those samples 1070A-1070*n* are placed on respective workpieces 400A-400*n*. Those workpieces 400A-400*n* are placed in one or more cassettes 102AA in a predetermined ordered sequence that embodies, e.g. the structure of the specimen 1070. As may also be realized, in one aspect, the ordered sequence of samples 1070S1-1070Sn or workpieces 400A-400*n* (e.g. a batch of samples) spans more than one cassette 102AA-102CC such as when one or more cassettes 102 are held within a magazine 105AA and the batch of samples 1070A-1070*n* or workpieces 400A-400*n* to be processed includes one or more of the cassettes 102AA-102CC in the magazine 105AA (e.g. the magazine 105AA holds one or more batches where the batches are identified by one or more of a workpiece identifying indicia and a cassette identifying indicia and correspond to, for example, a common structure or specimen). In another aspect the batch of samples including the ordered sequence of samples 1070A-1070*n* spans multiple magazines 105AA-105BB. In one aspect, the batch(es) (e.g. the workpieces/samples and/or cassettes included in the batches) are defined in a data structure DS (as described in greater detail below) by the workpiece identifying indicia and/or cassette identifying indicia (e.g. the batch to which a workpiece/sample belongs is included in the identifying indicia of a respective workpiece/sample). In one aspect the data structure is resident or embodied in a memory 199M of the controller 199 (for inclusion in, for example, the laboratory information management system LIMS) and is implemented as any suitable database such as, for example, an XML database, a relational database, an object-relational database, or any other database or data structure suitable for storing information as described herein.

In one aspect the pockets 500 of the cassette 102 are configured with tapered sides or guide members 500T. In one aspect the sides 500T direct the workpieces 400 into a holding slot 500S. In other aspects the tapered sides or guide members 500T are configured to allow gripper access into the holding locations for gripping the workpieces 400 (see FIG. 3I) and to allow viewing of the workpieces within the slots 500S with the workpiece detecting member 280. As may be realized, in one aspect, also referring to FIGS. 3D and 3J the pockets 500 include any suitable workpiece retaining features or structures 500R that are separate and distinct from or integral with one or more of the holding slot 500S and/or sides 500T of the pocket 500. The workpiece retaining features 500R may be configured to substantially prevent the workpieces from falling out of a respective pocket 500 due to, for example, accelerations, gravity or impacts while allowing (e.g. the retaining features 500R do not inhibit) extraction and insertion of the workpiece from and to the pocket 500 by the end effector 101, 301. Examples of workpiece retaining features 500R include, but are not limited to, grip tape, pressure sensitive adhesive, sheet adhesives, dispensed liquid adhesives (that dry or cure to form the retaining features), resilient members, electrostatic retention members, clips, stiction generating surfaces (e.g. coatings or applique/tape, surface patterns formed on a base material such as the cassette surface), non-slip surfaces with a friction/stiction grid formed thereon or any other suitable retention member(s). As may be realized, the retaining features 500R retain the workpieces 400 in the pockets 500 up to, for example, several G's of load in any direction, while allowing the end effector 101 or manually operated tweezers to be inserted into the pocket for extracting the workpieces 400 from the respective pockets 500 without any residue being left on the workpieces 400. As may also be realized, the workpiece retaining features 500R are configured to maintain a rotational position/orientation of the workpiece 400 while the workpiece is disposed within the pocket 500. For example, if the workpiece is inserted into the pocket with a predetermined rotational orientation (such as after being aligned with any suitable aligner (which in one aspect is external to the process module PM and/or automated transport and positioning system 100) that rotational orientation is maintained within the process module PM and/or automated transport and positioning system 100 so that the alignment of the workpiece 400 with the pre-aligner 103 may be skipped resulting in increased throughput in the process module PM. In other aspects, where the workpiece 400 is aligned with the pre-aligner 103 that rotational orientation is maintained within the pocket 500 by the workpiece retaining features 500R during transport of the workpiece within the cassette 102. In one aspect the workpiece retaining features 500R are high-vacuum compatible where a high vacuum is, for example, $10^{-5}$ Torr or below.

As may be realized, the cassette 102 may include any suitable kinematic locating features on one or more surfaces of the cassette 102 to allow relative positioning (e.g. alignment) between the pockets 500 (and workpieces therein) and the gripper of the end effector 101. For example, the first surface or side 102T includes one or more kinematic recesses 510 (or other suitable features) and a second surface or side 102B includes one or more recesses 511 (e.g. located at or adjacent one or more of the longitudinal sides SL3, SL4) that interface with the gripper 126G of the cassette shuttle 126 (FIG. 1D) for automated picking and placing the cassette 102 from and to the magazine 105. In one aspect the cassette 102 also includes recesses 515 on, for example, the lateral sides SL1, SL2 for allowing manual removal and insertion of the cassette 102 from and to the magazine 105. In other aspects the gripping features 515, 510, 511 are located at any suitable location of the cassette 102. In one aspect the lateral sides SL1, SL2 of the cassette 102 are also configured in any suitable manner to interface with the magazine 105, as will be described below, so that the cassette is inserted into the magazine 105 in a predetermined orientation. In one aspect, the lateral sides SL1, SL2 are tapered for engaging tapered surfaces 600T of the magazine 105 (FIG. 4A-4E) so that the cassette can only be inserted into the magazine 105 in a single orientation. In other aspects the cassette 102 engages the cover 590 (described below) where the cover 590 in turn engages the magazine such that both the cover and cassette have a nested "poka-yoke" or position determining features that provide for the insertion of the cassette/cover assembly into the magazine in the predetermined orientation. In one aspect a recess 520 is located on the second side 102B of the cassette 102 and includes any suitable wireless identification, such as RFID chips or other wireless identification, transponder, or telemetry unit. In other aspects the wireless identification is attached to the cassette at any suitable location and in any suitable manner.

Figure 3C:
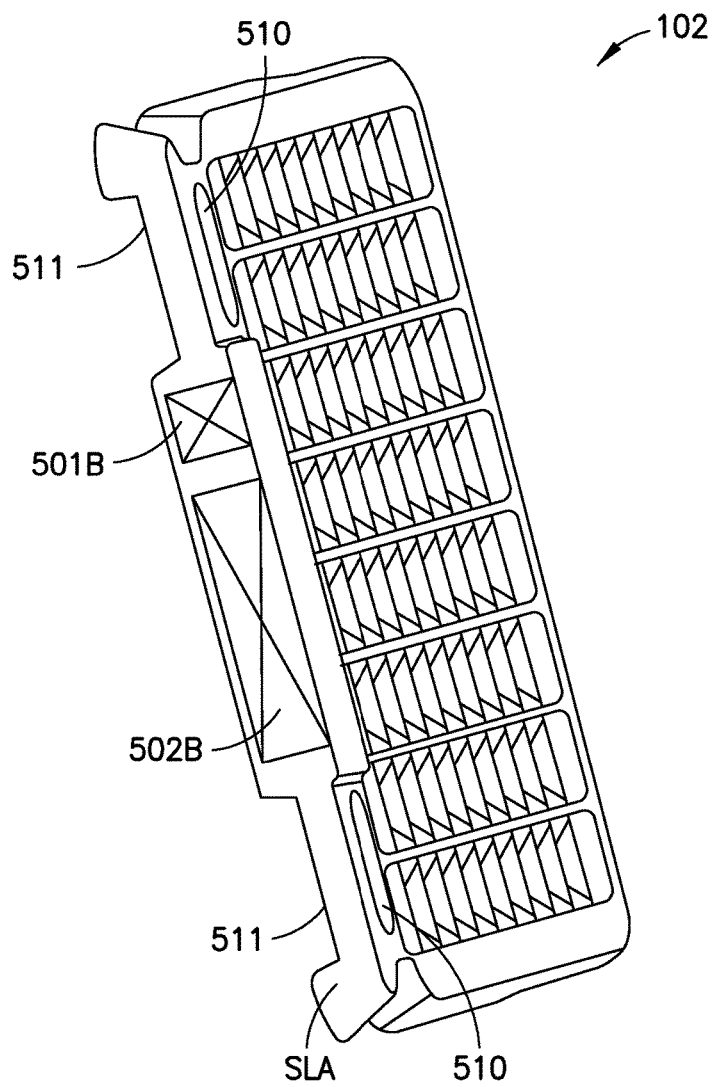
Figure 3D:
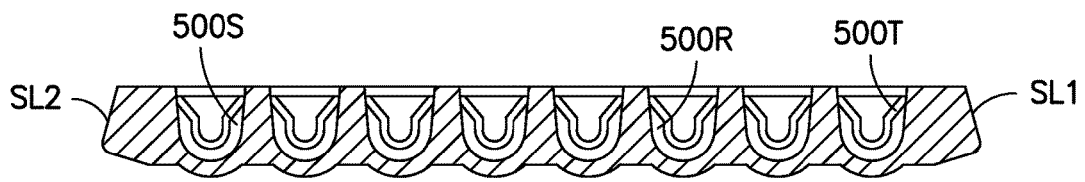
Figure 3H:
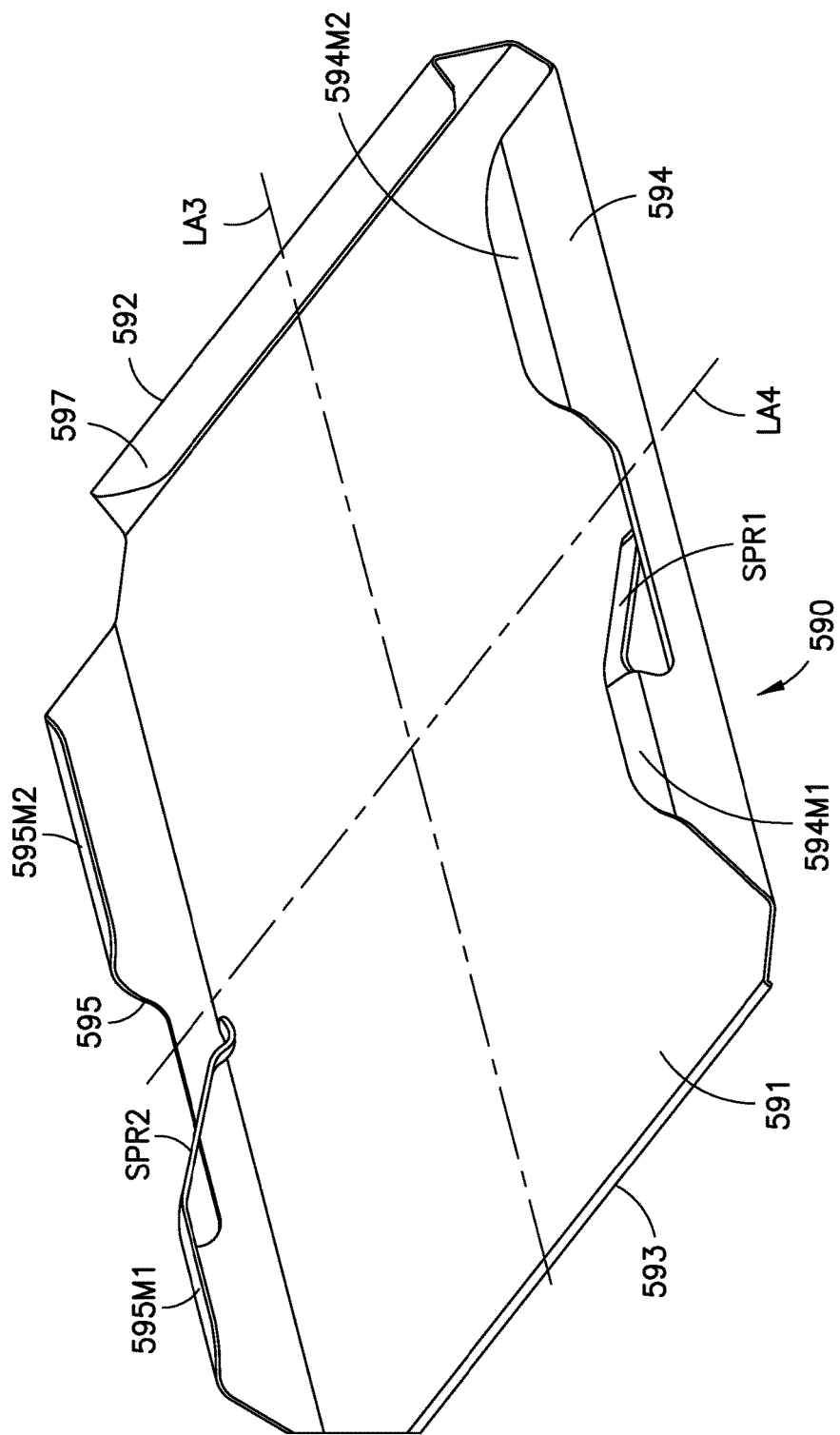
FIG. 3H is a schematic illustration of a portion of the specimen positioning system of FIGS. 1A-1D and the specimen cassette of FIGS. 3A-3G and 3I in accordance with aspects of the disclosed embodiment.
Figure 4F:
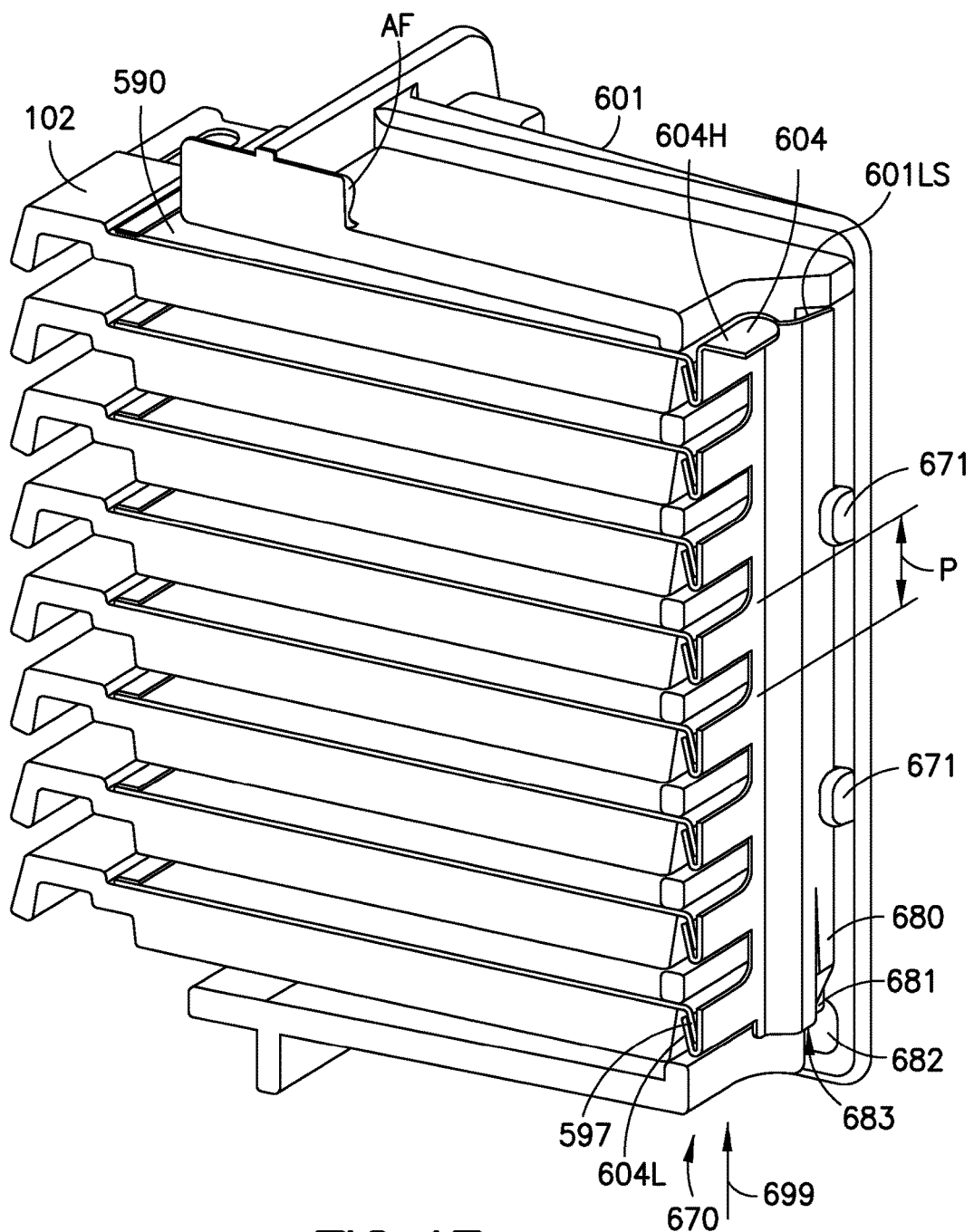

Referring also to FIGS. 3H and 3G the cassette 102, in one aspect, includes a detachable cover 590 for securing or otherwise retaining the workpieces 400 inside the pockets 500 during, for example, transport and/or storage of the cassette 102. The cover 590 has a longitudinal axis LA3 and a lateral axis LA4 so as to define longitudinal sides 592, 593 and lateral sides 594, 595. At least one longitudinal side 593 of the cover 590 is open to allow the cover 590 to slide over the cassette 102. For example, side 593 of cover is slid over the cassette 102 by moving the cover 590 from longitudinal side SL3 of the cassette 102 towards longitudinal side SL4 of the cassette as can be seen in FIG. 3G so that retaining surface 591 of the cover 590 is disposed adjacent to and spans the first side 102T of the cassette 102 for retaining the workpieces in their respective pockets 500. As may be realized the lateral sides 594, 595 of the cover extend or wrap around lateral sides SL1, SL2 of the cassette 102 (e.g. following the angle of the lateral sides SL1, SL2, for orienting the cassette in the magazine) so that extension members 594M1, 594M2, 595M1, 595M2 extend over a portion of the second surface 102B to substantially prevent separation of the cover 590 from the cassette 102. At least one extension member 594M1, 594M2, 595M1, 595M2 include resilient members SPR1, SPR2 that are configured to engage protuberances 537 disposed on the second side 102B of the cassette to substantially prevent relative longitudinal motion between the cassette 102 and the cover 590 and so that the cassette 102 is retained within the cover 590. It is noted that the retention force of the resilient member SPR1, SPR2 is such that it holds the cassette within the cover while allowing the cassette shuttle 126 to remove and insert the cassette 102 from the cover 590 and hence the magazine 105 as described herein. In one aspect the cover 590 also includes a locking member 597 at one of the longitudinal sides 592 for holding the cassette 102 and cover 590 assembly within the magazine 105 and to retain the cover 590 within the magazine 105 when the cassette shuttle 126 removes the cassette 102 from the magazine 105.

Referring to FIGS. 4A-4F a magazine 105 is illustrated in accordance with aspects of the disclosed embodiment. The magazine 105, together with one or more cassettes 102 forms a workpiece 400 storage system that is configured for manual or automated transfer of workpieces 400 to and from the pockets 500 of the cassettes 102 as described herein. The magazine 105 is configured to store at least one cassette 102, such as for example, 8 cassettes to allow for a workpiece holding capacity of 1,024 workpieces in a magazine where the cassette includes an 8×16 array of pockets. In other aspects the magazine holds more or less than 8 cassettes and has any suitable workpiece holding capacity in combination with the cassette(s). The magazine 105 includes a frame 601 that contains and supports the cassettes 102 as a unitary assembly. In one aspect the frame forms a cavity configured to be sealed with a door or cover and into which the cassettes are inserted for storage in any suitable environment of the cavity (such as for example, a vacuum environment, atmospheric environment, etc.). In other aspects the frame may not have a sealable cavity. The frame 601 includes any suitable kinematic features 610-612 (and/or automated handling features AF positioned in a known relationship with the kinematic features 610-612) that interface with corresponding kinematic features of the transport shuttle 120MS, as described above, for locating the magazine relative to the transport shuttle 120MS and/or for the automated loading of the magazine into, for example, the chamber 120C using any suitable automated magazine transport. In one aspect the kinematic features are pins and recesses but in other aspects the kinematic features are any suitable locating features. In one aspect the kinematic features 610-612 are also configured so that the magazine 105, when loaded on the transport shuttle 120MS has only a single predetermined orientation. In one aspect the frame 601 includes any suitable identifying indicia 620 (e.g. readable data storage media), that is/are substantially similar to the barcodes, human readable indicia, RFID, transponder and telemetry devices describe above, for the manual or automated identification of the magazine 105. In one aspect the identifying indicia 620 comprise magazine identification data that relates the magazine and an array of workpieces 400 held on one or more cassettes disposed therein to a source material configuration (the source material configuration being described in greater detail herein, see e.g. FIG. 7B). In one aspect, the magazine identifier 620 is the form of an active or passive electronic chip such as an RFID chip, Bluetooth transmitter or other suitable wireless identifier configured to be read by any suitable scanner SCR disposed within, for example, the automated transport and positioning system 100 and/or within any suitable portions of the workpiece processing system or facility 100PS (described in greater detail below, see FIGS. 7 and 7A).

As described above, the magazine 105 includes one or more cassette holding stations 600. Each cassette holding station 600 includes sides 600T that conform to the cross section of the cassette and cover assembly so that the cassette and cover assembly can be inserted into the magazine 105 in only a single predetermined orientation. As also noted above, the cover 590 of each cassette 102 includes a locking member 597 that engages a corresponding locking feature of the magazine 105 for retaining the cover 590 (and the cassette 102) within the magazine 105. For exemplary purposes only, the frame 601 forms a track 670 into which a retaining or latch plate 604 is inserted. The track 670 is positioned on the frame 601 so that the longitudinal side 592 of the cover is positioned adjacent the track when the cover and cassette assembly is inserted into a respective cassette holding station 600. The track 670 includes one or more bearing surface 601LS and opposing retaining members 671. The one or more bearing surface 601LS and the respective retaining members 671 are spaced apart so that the retaining plate 604 can be inserted between the one or more bearing surface 601LS and the respective retaining members 671. The retaining plate 604 includes a handle 604H configured to allow sliding manipulation of the retaining plate 604 for insertion and removal of the retaining plate to and from the track 670. The retaining plate 604 also includes locking members 604L that engage the locking members 597 of the covers 590 when the retaining plate 604 is inserted into the track 670. For example, the retaining plate 604 is slid or otherwise inserted in the direction of arrow 699 into the track 670 between the one or more bearing surface 601LS and the respective retaining members 671. The locking members 601L of the retaining plate 604 face the direction of insertion 699 while the locking members 597 of the covers 590 face a direction opposite the direction of insertion 699 so that when the retaining plate 604 is fully inserted into the track (as will be described below) the locking members 597 substantially simultaneously engage the opposing locking members 601L.

In one aspect the retaining plate 604 includes one or more resilient member 680 and the frame 601 includes one or more detents 681 and cam members 682. The resilient member 680 is configured to engage the cam member 682 when moving in the direction of arrow 699 (e.g. during insertion of the retaining plate in the track) so that the resilient member 680 passes over the cam 682 to engage the detent 681 for maintaining the retaining plate 604 in a closed state (e.g. the covers are securely held by the retaining plate) when the resilient member 680 is engaged with the detent 681. The resilient member is biased towards the bearing surface 601LS so that the resilient member 680 engages the detent 681 substantially preventing removal of the retaining plate 604 from the track 670. The retaining plate 604 includes a slot or channel 683 into which a release tool (not shown) is inserted to lift the resilient member 680 over the detent 681 and cam member 682 allowing passage of the resilient member 680 over the detent 681 and cam member 682 for removing the retaining plate 604 from the track 670 and/or releasing of the covers 590 from the frame magazine 105. In one aspect the frame 601 also includes another detent 681' and cam 682' and the retaining plate 604 includes another resilient member 680' configured to substantially prevent the retaining plate 604 from moving more than one cassette pitch P when, for example, the resilient member 680 and the detent 681 are disengaged. As may be realized, the retaining plate 604 includes a slot or channel 683', similar to slot or channel 683, into which the release tool (not shown) may be inserted to lift the resilient member 680' over the detent 681' and cam member 682' allowing passage of the resilient member 680' over the detent 681' and cam member 682' for removing the retaining plate 604 where the retaining plate 604 is completely removed from the track 670.

The covers 590, cassettes 102 and magazines 105 are constructed of any suitable materials. In one aspect the covers 590, cassettes 102 and magazines 105 are constructed from a vacuum environment compatible material for use in vacuum environments. In other aspects the covers 590, cassettes 102 and magazines 105 are configured for use in any suitable environment.

In one aspect the one or more suitable structures or identifying indicia of the workpiece 400, described above, is a physical representation of a sample held on a respective workpiece 400. For example, one or more of the suitable structures or identifying indicia is a unique identifier that is associated with a data structure DS (FIG. 1A—as described further below) which in one aspect is resident in a memory 199M of any suitable controller 199 (as will be further described below).

Figure 5A:
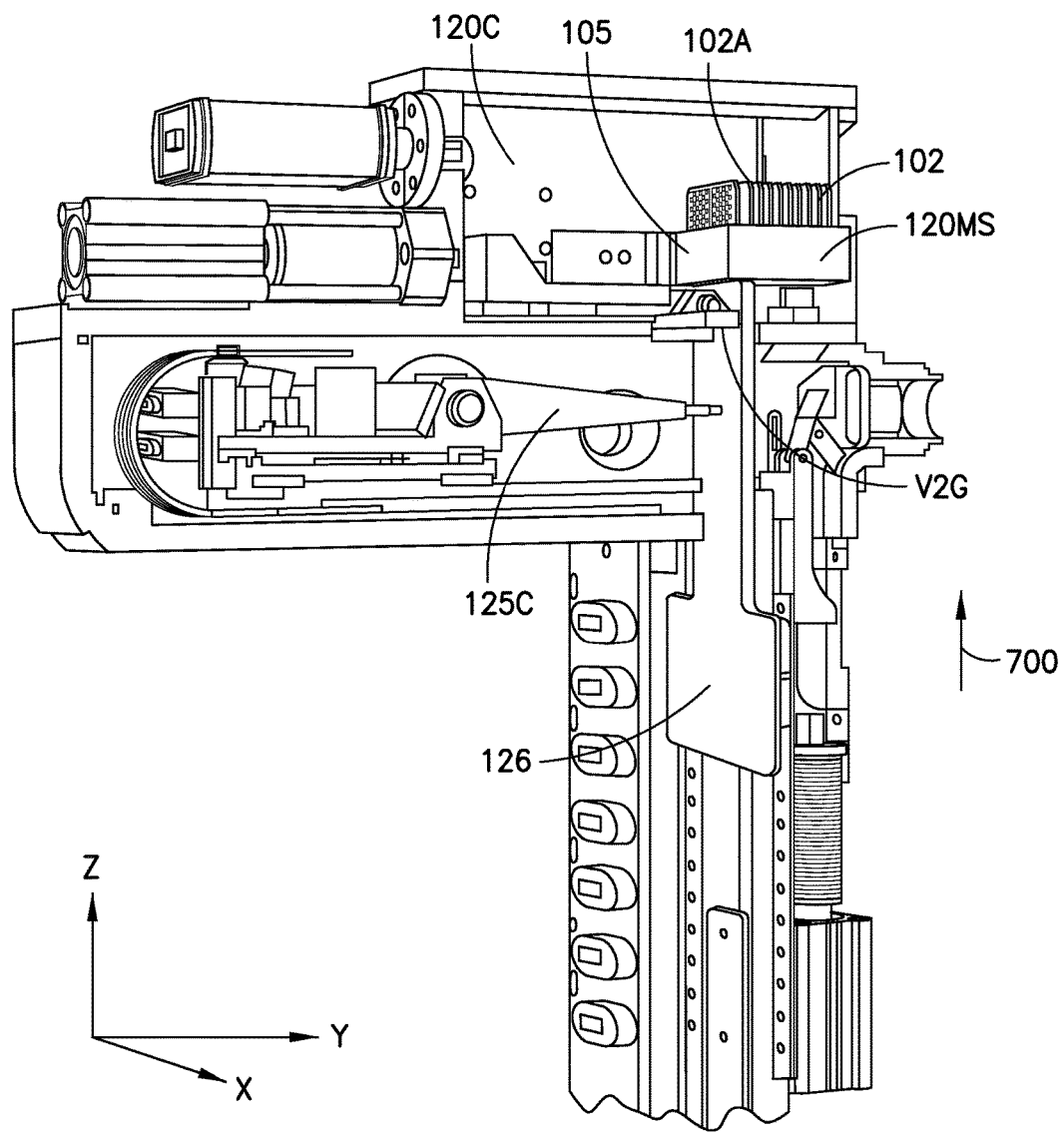
FIGS. 5A-5F are schematic illustrations showing an operation of the automatic specimen loading system of FIG. 1A in accordance with aspects of the disclosed embodiment.
Figure 5B:
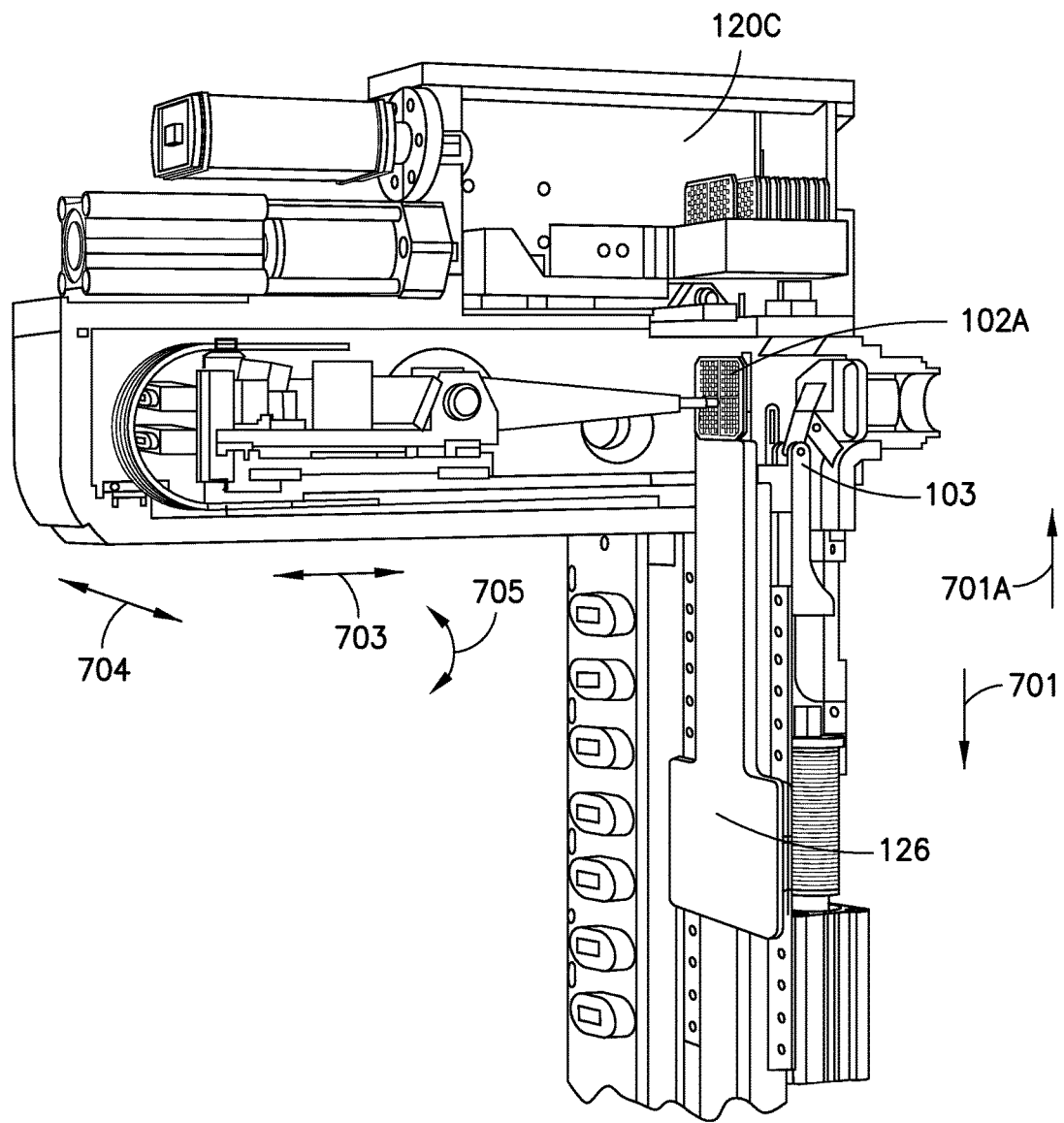
Figure 5C:
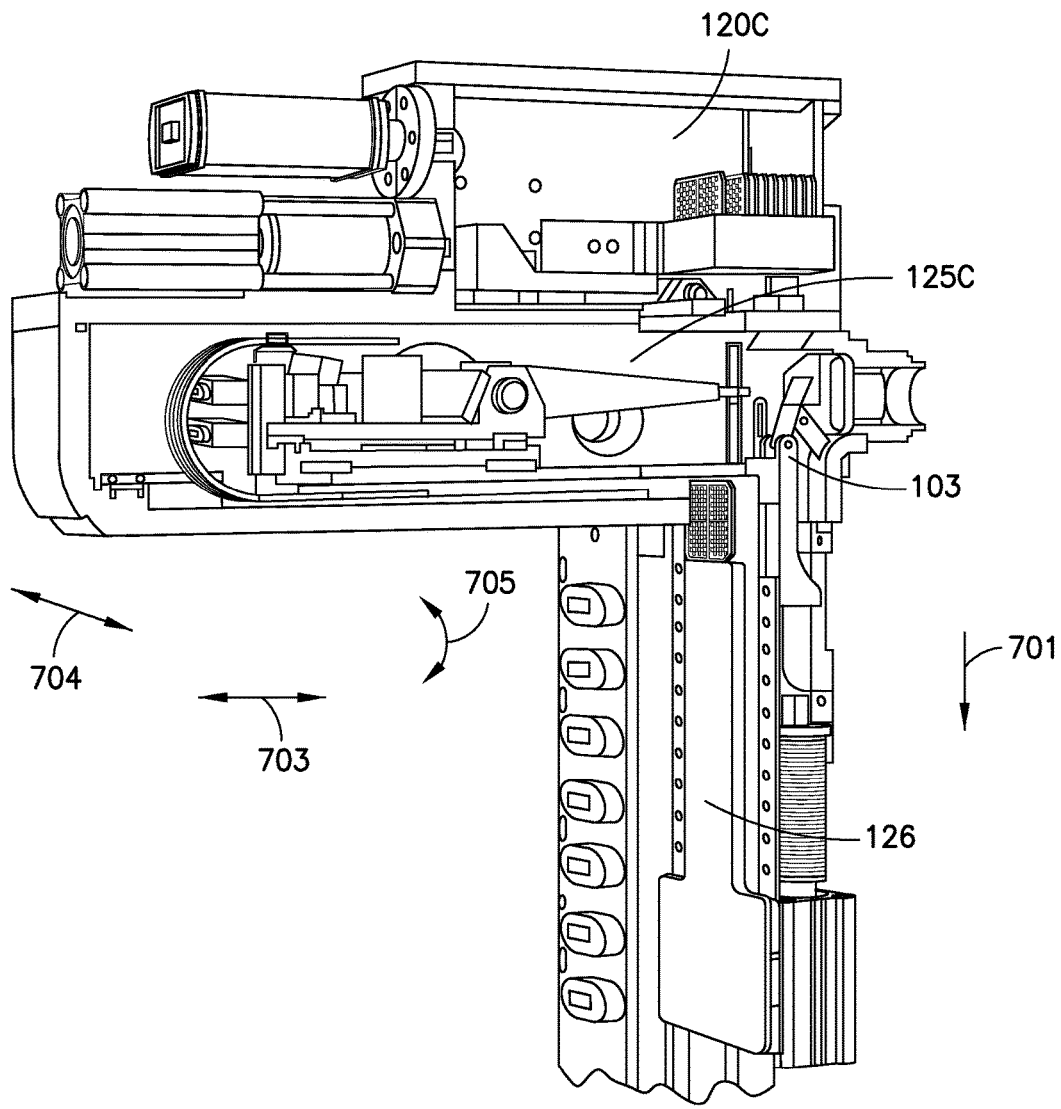
Figure 5D:
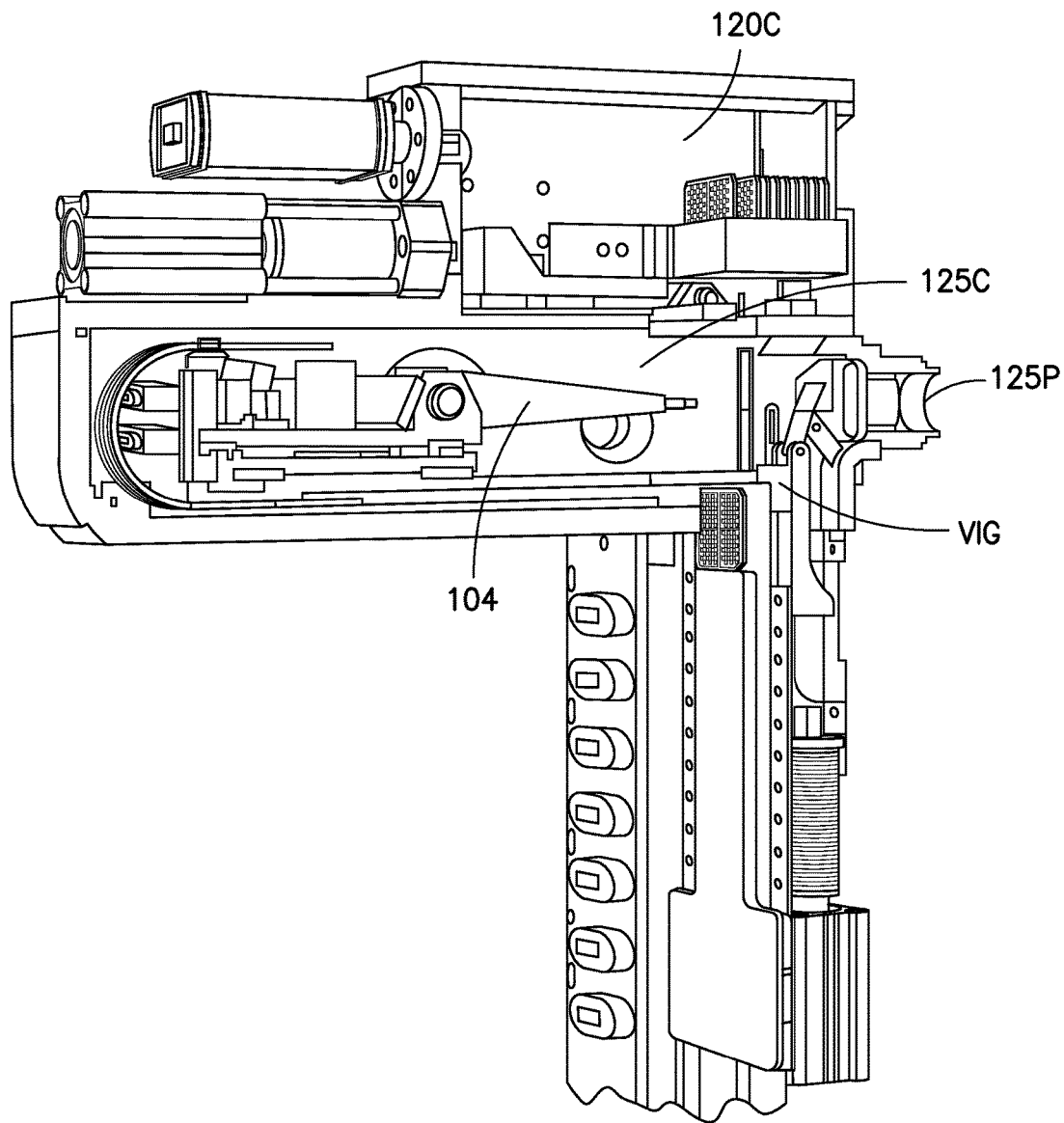
Figure 5E:
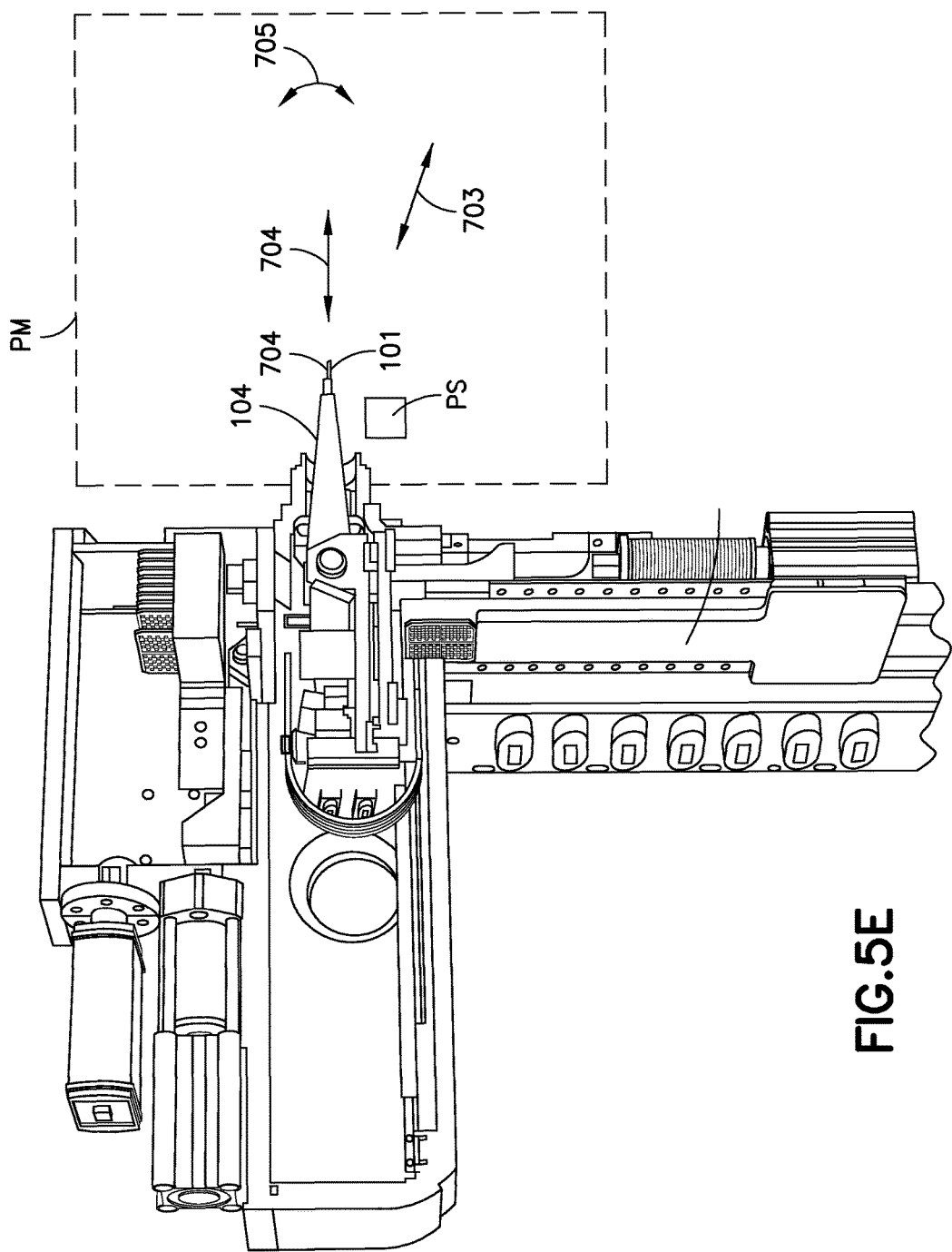
Figure 5F:
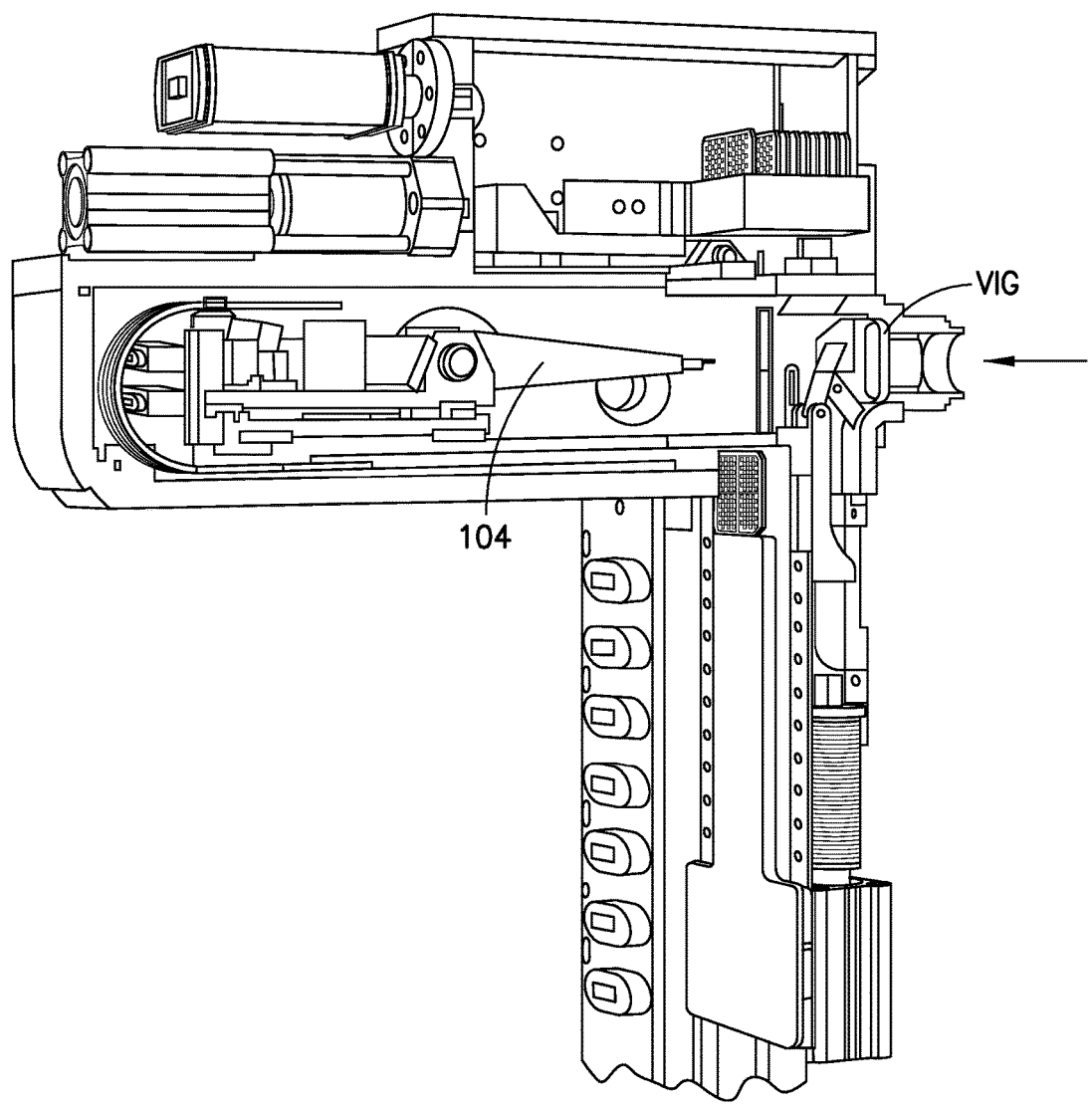
Figure 6:
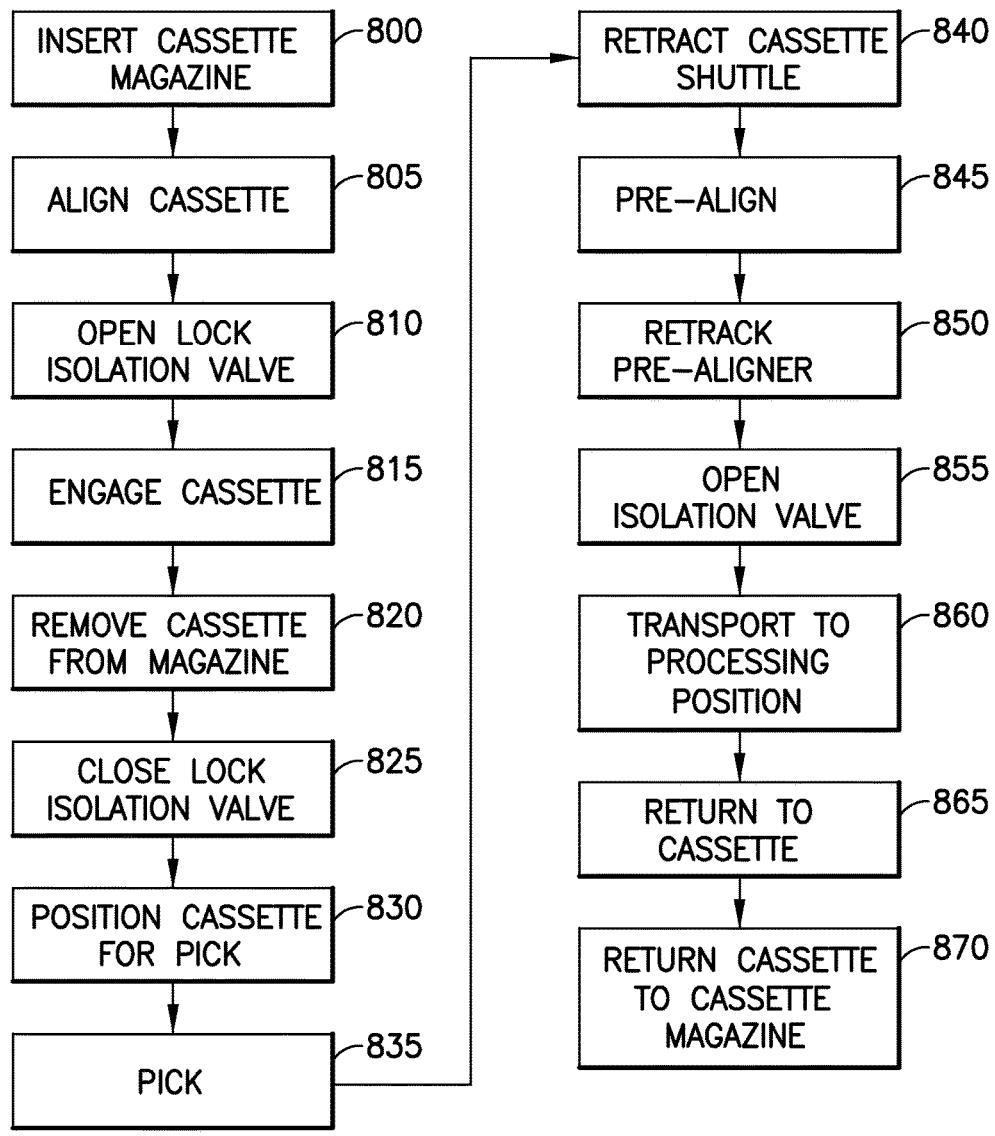
FIG. 6 is a flow diagram of an operation of the automatic specimen loading system of FIG. 1A in accordance with aspects of the disclosed embodiment.

Referring now to FIGS. 1A and 5A-5F an exemplary operation of the automated transport and positioning system 100 will be described in accordance with an aspect of the disclosed embodiment. The chamber 125C is pumped to a pressure substantially equal to a pressure of the process module PM and a magazine 105 holding one or more cassettes 102 is inserted into the sealable chamber 120C of the load lock 120 (FIG. 6, Block 800). For example, the door 120D is opened and the magazine 105 is kinematically placed on the transport shuttle 120MS in any suitable manner, such as manually or with any suitable transport automation. The door 120D is closed to seal or otherwise isolate the sealable chamber 120C. The load lock is pumped to a pressure compatible with or substantially equal to the pressure within the chamber 125C and the transport shuttle 120MS is moved to align a predetermined cassette 102A over the valve V2G (FIG. 6, Block 805). The valve V2G is opened so that the interior of the chamber 120C is in communication with the interior of the chamber 125C (FIG. 6, Block 810). The cassette shuttle 126 moves in the direction of arrow 700 to kinematically engage the predetermined cassette 102A (FIG. 6, Block 815). The cassette shuttle 126 moves in the direction of arrow 701 to remove the cassette 102A from the magazine 105 (and its respective cover 590) such that a predetermined workpiece is located within a range of motion of the workpiece positioning unit 104 (FIG. 6, Block 820). As may be realized, in one aspect, the positioning of the cassette 102A (and the workpieces therein) relative to the workpiece positioning unit 104 corresponds to a predetermined batch workpiece processing sequence (defined by or in the data structure DS—see FIG. 1A) of the batch of workpieces held on one or more cassettes 102 of the magazine 105 held on the magazine shuttle 120MS. The valve V2G is closed (FIG. 6, Block 825). The workpiece positioning unit 104 moves in one or more of the directions 703, 704, 705 (e.g. X, Y and tilt) for positioning the end effector 101 to pick a workpiece 400 from the cassette 102 (FIG. 6, Block 830) and picks the workpiece from the cassette 102 (FIG. 6, Block 835). The cassette shuttle 126 moves further in the direction of arrow 701 to move the cassette to a buffered position (FIG. 6, Block 840) and the workpiece positioning unit 104 moves in one or more of the directions 702, 704, 705 to place the workpiece 400 on the pre-aligner stage 103 for aligning the workpiece to a predetermined orientation (FIG. 6, Block 845). As may be realized, in one aspect, data obtained by the pre-aligner stage 103 regarding the alignment of the workpiece 400 is communicated to the controller 199 in any suitable manner for inclusion in the data structure DS. In one aspect the pre-aligner stage 103 is retracted in the direction of arrow 701 such as when the pre-aligner stage is movably mounted to the frame 140F independent of the cassette shuttle 126 (FIG. 6, Block 850). In other aspects where the pre-aligner stage 103 is mounted to the cassette shuttle 126 (so that the pre-aligner stage and cassette shuttle move as a unit) the cassette shuttle is retracted after alignment of the workpiece. In still other aspects the pre-aligner stage 103 is stationary along the Z axis and may not be retracted (e.g. the pre-aligner stage is positioned to allow workpiece positioning unit 104 access to the process module PM). The valve V1G is opened to allow access to the process module through port 125P (FIG. 6, Block 855). The workpiece positioning unit 104 moves in one or more of the directions 703, 704, 705 (e.g. X, Y, Z and tilt where tilt includes the alpha tilt axis TX and beta tilt axis TX2 as described in U.S. patent application Ser. No. 14/538,391 entitled "Workpiece Transport and Positioning Apparatus" and filed on Nov. 11, 2014 the disclosure of which is incorporated herein by reference in its entirety) for positioning the workpiece 400 within the process module PM for processing (FIG. 6, Block 860) while, in one aspect, being held by the end effector 101 or, in other aspects, on a positioning stage PS of the processing module PM. For example, where the workpiece 400 is processed on and positioned by (e.g. during processing) the positioning stage PS, the workpiece positioning unit 104 places the workpiece 400 on the positioning stage PS so that the positioning stage PS positions the workpiece within the processing module PM for processing. In one aspect, workpiece processing instructions are communicated to the process module (and/or an operator of the process module) by the controller 199 from the data structure DS to effect the processing of the workpiece 400 by the process module PM. In one aspect, processing data obtained during the processing of the workpiece 400 is communicated by the processing module PM to the controller for inclusion in the data structure DS. The workpiece positioning unit 104 retracts from the process module PM and the valve V1G is closed (FIG. 5F). The cassette shuttle 126 moves in the direction of arrow 701A to position cassette 102 so that the workpiece positioning unit 104 returns the workpiece 400 to the pocket 500 in the cassette 102 from which the workpiece was taken (FIG. 6, Block 865). As may be realized, in one aspect additional workpieces held by the cassette 102 are processed, such as in the predetermined batch workpiece processing sequence noted above, before the cassette 102 is returned to the magazine 105. The valve V2G is opened and the cassette shuttle 126 returns the cassette 102 to the magazine 105, the valve V2G is closed and the transport shuttle 120MS moves to a predetermined position for removal of the magazine from the chamber 120C (FIG. 6, Block 870). In other aspects the transport shuttle 120MS aligns a different cassette 102 with the valve V2G for processing of another workpiece (or multiple workpieces, e.g. a batch of workpieces held by the different cassette) and/or for continuing the processing of a batch of workpieces that is defined in more than one cassette 102.

As noted above, the controller 199 includes a data structure DS that effects tracking and analysis of specimens located on one or more workpieces. In one aspect, the controller 199 includes a neural network and/or a state machine that are configured to create and maintain the data structure DS while in other aspects the controller includes any suitable processing/processor configured to create and maintain the data structure DS. In one aspect the neural network and/or state machine is/are configured to control operations and a process flow of the automated transport and positioning system 100 (e.g. such as routing of automated transports, which workpieces are delivered to which process modules and in which order, process scheduling and/or process sequence control of the workpieces, etc.), as described herein, based on information in the data structure DS. The data structure, as described herein, includes data regarding where the workpieces 400 have been throughout, for example, a laboratory or other facility (as will be described below) from the time the samples are placed on workpieces to obtaining final results of analysis of the samples as well as detailed data regarding the processes performed on the samples. In one aspect the controller 199 includes a user interface configured to allow a user to view the results of the analysis or any other data within the data structure DS including a location of a sample within the laboratory or other facility.

In one aspect the data structure DS includes information pertaining to a batch of workpieces/specimens that are processed through the automated transport and positioning system 100, process module PM or any other suitable laboratory equipment configured to store, transport and/or analyze the workpiece/specimen. As may be realized, any suitable structure or specimen 1070 (e.g. source material), such as a biological structure, metallurgical structure, semiconductor structure, etc.) is divided into samples in any suitable manner where each sample is mounted to a respective workpiece 400 in any suitable manner. As each sample is associated with a workpiece 400 (e.g. a sample is mounted to the workpiece) the data structure DS is updated so that the data structure DS associates one or more predetermined characteristic/physical attribute of the sample with the unique identifier of the workpiece 400. As may be realized, the data structure DS also associates samples taken from a common structure 1070 with each other so that the individual samples (which are associated with the workpieces) are tracked and analyzed as whole so that an automatic determination of a characteristic of the structure 1070 is made with respect to the structure 1070 as whole (as will be described in greater detail below).

Referring to FIGS. 7, 7A and 7B, in one aspect, the automated transport and positioning system 100 is part of or integrated in workpiece processing system 100PS. The workpiece processing system is, in one aspect, located within any suitable facility or enclosure 73 that has for example walls 73A, 73B, 73C, 73D connected to each other by a floor 74 and a ceiling/roof (not shown). An access door AD is provided for the enclosure 73 to allow operator access into the enclosure 73 for any suitable reasons. The workpiece processing system or facility 100PS includes, for exemplary purposes only, one or more sample preparation modules 1000, one or more workpiece sequencer modules 1099, one or more automated magazine loaders 1002, one or more automated transport and positioning systems 100 (and the respective processing modules PM), one or more storage modules 1069 and one or more automated transports 1001 all of which are, in one aspect connected to the controller 199 in any suitable manner (e.g. such as through a wired or wireless connection). In one aspect the one or more automated transports 1001 form front loading automation that loads/removes workpieces 400 and/or cassettes 102 to/from one or more workpiece sequencer modules 1099, loads/removes cassettes and/or magazines 105 to one or more automated magazine loaders 1002 and loads/removes magazines 105 to/from one or more automated transport and positioning systems 100. In one aspect, one or more of the facility 73, sample preparation modules 1000, workpiece sequencer modules 1099, automated magazine loaders 1002, automated transport and positioning systems 100 (and the respective processing modules PM), storage modules 1069 and automated transports 1001 include any suitable temperature controls for maintaining the sample specimens held on the workpiece at a predetermined temperature. In one aspect, the specimen samples are maintained at, for example, cryogenic temperatures while, in other aspects, the specimen samples are maintained at any suitable temperature by the one or more of the facility 73, sample preparation modules 1000, workpiece sequencer modules 1099, automated magazine loaders 1002, automated transport and positioning systems 100 (and the respective processing modules PM), storage modules 1069 and automated transports 1001. As may be realized, the magazines 105 and cassettes 120 are also, in one aspect, configured in any suitable manner for maintaining the specimen samples at the predetermined temperature. For example, the cassettes 102 and magazines 105 are, in one aspect, configured heat sinks for maintaining a temperature of the specimen samples. In other aspects, the magazine 105 and/or cassette 102 includes a sealed and cooled environment in which the specimen samples (e.g. on the workpieces) are located.

The one or more automated transports 1001 include magazine transport units 1001A and cassette transport units 1001B that are configured to travel along a common set of tracks 1001T. In other aspects, there is a set of tracks for the magazine transport units 1001A that are separate and distinct from a set of tracks for the cassette transport units 1001B. In one aspect the magazine transport units 1001A include any suitable gripper 1001AG for gripping the automated handling features AF of the magazines 105 (see e.g. FIGS. 4A-4E) and transporting the magazines 105 (with or without cassettes 102 located therein) between the automated magazine loaders 1002, the automated transport and positioning systems 100 and the storage modules 1069 where kinematic features 610-612 of the magazine locate the magazine 105 in the automated transport and positioning systems 100 and the storage modules 1069. The cassette transport units 1001B include any suitable gripper 1001BG for gripping the automated handling/kinematic features 510, 511 of the cassettes 102 (see e.g. FIGS. 3A-3F) and transporting the cassettes 102 between the workpiece sequencer modules 1099 and the automated magazine loaders 1002 the where kinematic features 510 of the cassettes 102 are positioned relative to a datum surface, such as a side of the cassette for locating the cassette 102 in the workpiece sequencer modules 1099 and the automated magazine loaders 1002. In one aspect, a common automated transport unit is configured to grip both the automated handling features AF of the magazines 105 and the cassettes automated handling/kinematic features 510, 511 of the cassettes 102 for transporting either one of the magazines 105 and cassettes 102 between any suitable locations of the workpiece processing system 100PS. In one aspect, the one or more automated transports 1001 include any suitable transport for transporting workpieces between the sample preparation modules 1000 and the workpiece sequencer modules 1099. In one aspect the automated transports 1001 are an overhead material handling system while in other aspects the automated transports 1001 are conveyors or any other suitable mechanized transport. As may be realized, the transport of the cassettes 102 and magazines 105 can also be performed manually.

The sample preparation modules 1000 are any suitable modules configured to prepare a sample 1070S1-1070Sn (generally 1070S) from a structure or specimen 1070 and place that sample on a workpiece 400A-400n (generally 400). It is noted that, each of the sample preparation modules 1000 includes any suitable vision systems 1000V (which in one aspect are similar to vision system 1080V described herein) that are configured to send suitable identification signals to the controller 199 that identify, for example, a workpiece 400 on which a particular sample 1070S is mounted or any other suitable information that effects population of the data structure DS as described herein. In other aspects the specimen/workpiece relational is obtained and transmitted to the controller 199 for inclusion in the data structure DS in any suitable manner.

The workpiece sequencer modules 1099 are connected to one or more sample preparation modules 1000 in any suitable manner so that samples 1070S disposed on workpieces 400 are transferred therebetween. The workpiece sequencer module 1099 illustrated in FIG. 7 is exemplary only and it should be understood that the workpiece sequencer module 1099 includes any suitable structure, features and/or components for transferring workpieces 400 with samples 1070S thereon from any suitable sample preparation module 1000 to one or more cassettes 102 where the workpieces 400 are placed in the cassette(s) 102 in a predetermined ordered sequence (see FIG. 7B) such as that described above so that the predetermined ordered sequence embodies the structure of the specimen/structure 1070. For exemplary purposes only, the workpiece sequencer module 1099 includes a frame 1099F, a cassette holder 1098 mounted to the frame 1099F and an automated workpiece transport 1090 mounted to the frame 1099F. The cassette holder 1098 is configured to hold one or more cassettes 102 in any suitable manner so that an automated transport 1001 (such as a cassette transport unit 1001B) transfers the one or more cassettes 102 between the cassette holder 1098 and, for example, an automated magazine loader 1002. In one aspect the cassettes 102 are kinematically located in the cassette holder 1098 in any suitable manner (e.g. at least one side of the cassette proves a datum seating surface for locating the workpiece holding pockets 500 where the datum seating surface is in a known relationship with the automated handling/kinematic features 510, 511 of the cassettes 102) so that workpiece holding pockets 500 of the cassettes are each located in a known position relative to, for example, the automated workpiece transport 1090.

Figure 7C:
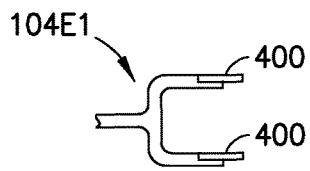
FIGS. 7C and 7D are schematic illustrations of a portion of a processing system in accordance with aspects of the disclosed embodiment.
Figure 7D:
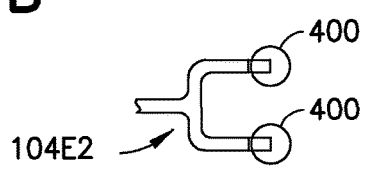

In one aspect the automated workpiece transport 1090 includes at least three degrees of freedom (along e.g. the X, Y and Z axes) for picking and placing workpieces between the sample preparation module 1000 and the cassettes 102 while in other aspects the automated workpiece transport 1090 includes more or less than three degrees of freedom. For example, the automated workpiece transport 1090 includes a Y axis stage 1010, an X axis stage 1011 and a Z axis stage 1012 to which a workpiece holder 1004 is mounted for movement in at least the X, Y and Z directions. In one aspect the automated workpiece transport 1090 includes one or more rotational axes RA1, RA2 that enable the workpiece holder 1004 to rotate and pick/place workpieces from any suitable workpiece holding stations (e.g. such as the sample preparation module 1000, other cassette holders, etc.) in multiple parallel and/or perpendicular planes. The workpiece holder 1004 includes any suitable end effector 1004E configured to grip and hold a workpiece 400, which in one aspect is substantially similar to end effector 101 described above. In one aspect, the end effector 1004E is a multiple workpiece holding end effector. For example, referring to FIGS. 7C and 7D the end effectors 104E1, 104E2 are respectively configured to hold two workpieces 400 one over the other in a stack or side by side in a common plane. As may be realized, the end effectors 104E1, 104E2, in other aspects, are configured to hold any suitable number of workpieces in any suitable spatial arrangement relative to one another. As may also be realized, the spacing between the workpieces on the end effectors 104E1, 104E2 is substantially the same as the spacing of the pockets 500 of the cassette 102 for allowing substantially simultaneous picking/placing of workpiece from/to the cassette 102 or any other suitable workpiece holding locations.

In one aspect the workpiece sequencer module 1099 includes any suitable vision system 1080V that includes one or more sensors 1080 for imaging or otherwise detecting (e.g. in one aspect the vision system includes other suitable optical and/or radio frequency readers), for example, one or more of locating features (such as the fiducials 404A-404D) and unique identifiers (such as barcodes 402A, 402B and/or identifier 403) of the workpieces 400 (see e.g. FIG. 2A) to effect handling of the workpiece 400 with the automated workpiece transport and/or identification of the workpiece 400 and sample 1070S held thereon (e.g. with respect to the data structure DS as described below). In one aspect the one or more sensors 1080 are CCD cameras or other imaging device configured to read or recognize the fiducials 404A-404D, barcodes 402A, 402B and/or identifier 403. The one or more sensors 1080 are placed in any suitable position relative to, for example, the automated workpiece transport 1004, cassettes 102 and/or the sample preparation module 1000 so that suitable identification signals are sent from the vision system 1080V to the controller 1099 upon viewing of the workpiece 400 held by, for example, the end effector 1004E of the automated workpiece transport 1004.

As noted above, the automated transport 1001 is configured to transport the cassettes 102 between the cassette holder 1098 and the automated magazine loader 1002. As may be realized, the automated transport 1001 is also configured to transport the cassettes 102 (which are located within the magazine(s) 105) to the automated transport and positioning system 100.

In one aspect, the data structure DS includes data fields that associate descriptors with the unique identifier of the workpiece 400 such as, for example, an identification of a sample 1070S located on the workpiece 400, one or more of a specimen/sample type (e.g. what the specimen/sample is), a sample size, sample location/orientation relative to the workpiece and/or a workpiece holder/gripper, a sample sequence in a batch of samples (e.g. such as when the structure 1070 is divided into multiple samples for analysis), a location of the sample in a batch of samples, a specimen/sample source (e.g. from where, who and/or what the specimen was obtained), a predetermined batch workpiece processing sequence for workpieces in a batch of workpieces, instructions for processing the sample, analysis of a group of samples from a common specimen as a whole, a final destination of the sample or any other suitable characteristics/physical attributes of the specimen/sample. As may be realized, as the workpiece 400 and sample 1070S thereon is processed (e.g. from mounting of the specimen sample on the workpiece to final analysis and/or storage of the specimen) a process history that includes one or more of process steps and an event log for the workpiece is stored in the data structure DS for that sample and associated with a respective unique identifier for the respective workpiece 400.

Referring also to FIG. 1, as noted above, the controller 199 is configured to track each workpiece 400 (and the sample 1070S thereon) in a batch of workpieces/samples (which in one aspect is in a sequenced order) with the data structure DS. As an example, in one aspect, a structure or specimen 1070 (e.g. source material) is divided into multiple samples 1070S1-1070Sn by, for example, the sample preparation module 1000 (FIG. 8, Block 900). A workpiece 400 is picked or otherwise retrieved by an automated workpiece transport 1004A of, for example, the sample preparation module 1000. In other aspects the automated workpiece transport 1004 picks and positions a workpiece 400 in the sample preparation module 1000. The automated workpiece transport 1004, 1004A positions the workpiece 400 in proximity to any suitable reader (such as vision system 1000V or other radio frequency reader) and an identification of that workpiece is sent to the controller 199 (FIG. 8, Block 902). As the samples 1070S are placed on the respective workpieces 400 a change in status of the workpieces is recorded in the data structure DS and an association between the sample 1070S and the workpiece 400 is formed and any suitable identification data signals are transmitted to the controller 199 so that the sample 1070S placed on the workpiece 400 is associated with that workpiece 400 in the data structure DS (FIG. 8, Block 904). In one aspect the identification data signals are transmitted by the vision system 1000V (or other suitable reader) of the sample preparation module 1000 while in other aspects the identification data signals associating the sample 1070S with the workpiece 400 are transmitted by the vision system 1080V (or other suitable reader) during transport of the workpiece 400 (with the sample 1070S thereon) by the automated workpiece transport 1004. In other aspects, any suitable scanner SCR (of for example, vision system) reads passive or active media (e.g. RFID chips, Bluetooth transmitters, etc.) of the workpiece such that suitable data is transmitted to the controller 199 by the scanner SCR for forming the association between the sample 1070S and workpiece 400. As may be realized, the identifying indicia of the workpiece 400 provide for, along with the data structure DS, tracking each sample 1070S in a sequenced batch of samples throughout sample processing and for arranging the samples 1070S in a sequenced order based on the identifying indicia where process information for each sample 1070S (e.g. from mounting the sample to the workpiece 400 to an end result of sample analysis and/or storage) is linked to the respective identifying indicia in the data structure DS.

In one aspect, the controller 199 controls the automated workpiece transport 1004 so that the workpieces (and samples thereon) are placed within the pocket(s) 500 of one or more cassettes 102 in a predetermined sequence where the predetermined sequence and the data associated with the workpieces in the data structure DS embodies a structure of the structure 1070 being analyzed. The predetermined sequence in which the workpieces 400 are placed in the one or more cassettes 120 is based on any suitable criteria. For example, samples 1070S that are sequentially taken from a structure 1070 are placed in the one or more cassettes 102 in a predetermined order that corresponds with, for example, an order in which the samples 1070S were taken from the structure 1070. In one aspect one or more batches of samples are identified by the controller 199 based on, for example, a relationship between the samples (e.g. taken from a common structure 1070, etc.) or any other suitable criteria (FIG. 8, Block 905) where the batches are processed in a predetermined order or sequence as identified by the controller 199 and/or data structure DS. In other aspects the workpieces 400 (and the samples thereon) are placed in the pocket(s) 500 of the cassette(s) 102 in any suitable manner. Regardless of how the workpieces 400 (and samples thereon) are arranged in the cassette(s) 102, an association is made between the workpieces 400 and the cassette 102 in which the workpieces 400 are placed as (or prior to) each workpiece 400 in the batch of workpieces is loaded into one or more cassettes 102 (see e.g. FIG. 3I) in the manner described herein where a unique identifier (see e.g. barcode 501A in FIG. 3A) of the one or more cassettes 102 is associated with the unique identifier of the respective workpieces 400 in the data structure DS. For example, the automated workpiece transport 1004 moves a workpiece 400 (with sample 1070S thereon) from the sample preparation module 1000 to a location proximate vision system 1080V or other suitable reader of the workpiece sequencer module 1099 so that the workpiece 400 (and sample 1070S thereon) is identified for placement in a pocket 500 of a cassette 102 (FIG. 8, Block 907).

In one aspect the automated workpiece transport 1004 places the workpiece 400 in a predetermined cassette pocket 500 location, in the array of pockets of the cassette 102, (FIG. 8, Block 909). A status of the workpiece is updated so that each workpiece 400 is associated with the respective location of the pocket 500 so that the location of each workpiece relative to the kinematic features of the respective cassette is known (FIG. 8, Block 910). In one aspect, the controller 199 is configured to make the workpiece/cassette association and the workpiece/pocket association within the data structure DS and instruct the automated workpiece transport 1004 to place the workpiece 400 in the predetermined pocket 500 of a predetermined cassette 102. In other aspects, the vision system 1080V sends identification signals to the controller 199 indicating which pocket 500 of which cassette 102 a workpiece is placed based on the unique identifiers of the workpiece 400 as well as the cassette and pocket identifiers of the cassette 102 (as described above). As may be realized, where the controller 199 prescribes a pocket 500 in which the workpiece 400 is to be placed, the controller sends any suitable transport protocol to the automated workpiece transport 1004 for transporting the workpiece and the location of the workpiece in the cassette 102 is verified in any suitable manner, such as with vision system 1080V or scanner SCR (FIG. 8, Block 911). In one aspect, upon verification of workpiece placement in the cassette 102 a status of the workpiece is updated in the data structure to indicate the workpiece 400 is properly placed in the cassette 102.

The cassette 102 is picked or otherwise removed from the cassette holder 1098 in any suitable manner, such as by the automated transport 1001 (e.g. a cassette transport unit 1001B) where the cassette is brought in proximity with any suitable reader SCR for identifying the cassette (FIG. 8, Block 915) such that any suitable signals are sent from the scanner SCR to the controller 199 for updating a status of the workpiece 400 in the data structure DS (FIG. 8, Block 917). In one aspect, the controller 199 sends signals to the automated transport 1001B for transporting the cassette 102 to a predetermined cassette 105 (and in one aspect, a predetermined location within the cassette 105) within a predetermined automated magazine loader 1002. In one aspect the cassette is transported by any suitable scanner SCR or vision system 1002V of the automated magazine loader to verify a location of the cassette 102 at the automated magazine loader 1002 (FIG. 8, Block 918) and the cassette 102 is loaded into a magazine 105 in any suitable manner (FIG. 8, Block 919). For example, a magazine 105 is kinematically located in the automated magazine loader and the cassette transport unit 1001B is configured to insert the cassette 102 carried by the cassette transport unit 1001B into a respective holding slot of the magazine 105 where, as may be realized, the insertion of the cassette 102 into the magazine is effected by the kinematic locating features of the magazine and the cassette. As may be realized, in one aspect, covers 590 are predisposed within the magazine 105 and the cassettes 102 are inserted into the covers 590 so that the cassettes 102 are retained in the magazine 105. In other aspects the covers 590 are placed on the cassettes 102 (or vice versa) in any suitable manner prior to inserting the cassette 102 in the magazine 105. As may be realized, the magazine 105 is positioned within the automated magazine loader so that a unique identifier (see e.g. identifying indicia 620 in FIG. 4C) of the magazine 105 is read by any suitable reader SCR so that as the cassette 102 is placed within the magazine 105 a status of the workpieces 400 within the cassette 102 are updated in the data structure and the magazine 105 is associated with the unique identifier of the workpieces 400 loaded therein (FIG. 8, Block 920). As such, the data structure includes data indicating at least which magazine 105 the sample(s) is (are) located, in which cassette 102 (within the magazine 105) the sample is located, in which pocket 500 of the cassette 102 the sample is located and on which workpiece 400 the sample is located.

In one aspect, each automated magazine loader 1002 includes suitable vision systems 1002V (which in one aspect are similar to vision system 1080V described herein) that are configured to send suitable identification signals to the controller 199 that identify, for example, a magazine 105 in which a particular cassette (and hence a workpiece) is located, a position of the cassette 102 within the magazine 105 or any other suitable information that effects population of the data structure DS. In other aspects the magazine/cassette/workpiece relational data is obtained and transmitted to the controller 199 for inclusion in the data structure DS in any suitable manner. For example, any suitable scanner SCR reads passive or active media (e.g. RFID chips, Bluetooth transmitters, etc.) of the cassette and magazine such that suitable data is transmitted to the controller 199 by the scanner SCR for forming the association between the sample 1070S, workpiece, cassette and magazine.

Figure 9:
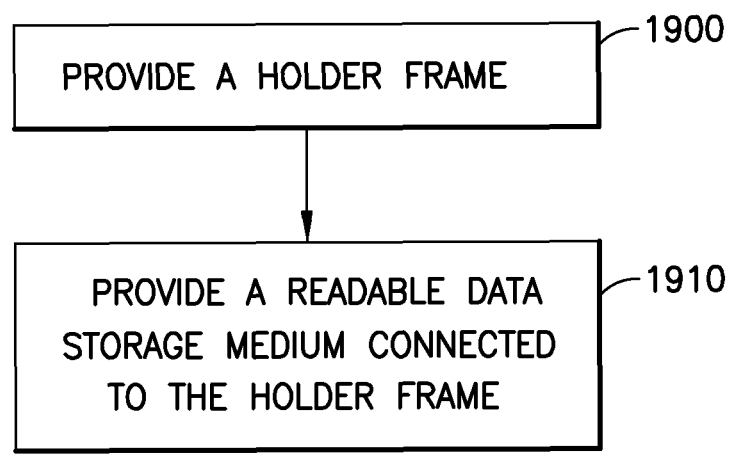
FIG. 9 is a flow diagram in accordance with aspects of the disclosed embodiment.

The magazine 105 picked from and transferred from the automated magazine loader 1002 such that any suitable data is sent to the controller 199 (by for example, scanner SCR of the automated transport 101 or automated magazine loader 1002 or vision system 1002V) for updating an in process location of the workpieces (FIG. 8, Block 925). In a manner substantially similar to that described above, in one aspect, the controller 199 prescribes a predetermined automated transport and positioning system to which the magazine is transported. The magazine 105 is loaded into the automated transport and positioning system 100 and the location of the magazine is verified by, for example, any suitable scanner SCR or vision system of the automated transport and positioning system 100 (FIG. 8, Block 926) where a status, such as the in process location of the magazine (and hence the specimens therein), is updated and recorded (e.g. an in process specimen sample location is updated) in the data structure DS (FIG. 9, Block 928). In one aspect the magazine transport unit 1001A transports the magazine to and loads the magazine on/in the automated transport and positioning system 100 while in other aspects the magazine 105 is transported to and loaded on/in the automated transport and positioning system 100 in any suitable manner. As may be realized, the in process location of the magazine, cassettes, and workpieces (and hence the samples), in one aspect, is updated in real time as the magazine, cassettes, and workpieces (and hence the samples) are moved around/within the facility 73 (which may be a laboratory), the automated transport and positioning system 100, process module PM or any other suitable workpiece holding location. For example, in one aspect, as described herein one or more of the sample preparation module 1000, automated magazine loader 1002, the workpiece sequencer module 1099 and the automated transport and positioning system 100 are in communication with the controller 199 and configured to read or otherwise identify the magazines, cassettes and workpieces located therein and communicate the same along with, for example, any processing data regarding processing performed on a sample, to the controller 199 to effect substantially real time updating of the sample process data within the data structure DS.

At least one cassette 102 is removed/picked from the magazine 105 by, for example, the cassette shuttle 126 and is transported by any suitable scanner SCR or vision system of the automated transport and positioning system so that the cassette 102 being removed or picked is identified and its location is verified with the controller (FIG. 8, Block 929). As may be realized, in one aspect the controller specifies which cassette is to be picked based on the cassette identifier and its location within the magazine 105 where the identification of the cassette 102 verifies that the specified cassette is picked. In other aspects the cassette 102 is picked and identified such that the controller 199 uses the identification of the cassette to specify a process/process order for the workpieces in the cassette 102. The identification of the cassette 102 that is removed from the magazine 105 also effects a change/updated status (e.g. in the data structure DS) of the workpieces in that cassette 102 where the change in status is a change in location of the workpieces, a change regarding an in process status of the workpieces or any other suitable data within the data structure is updated (FIG. 8, Block 930).

The automated transport and positioning system 100 picks one or more workpieces 400 from the cassette so as to cycle through the workpieces 400 held in one or more of the cassettes 102 of the magazine 105 in, for example, the predetermined batch workpiece processing sequence where the workpieces are each transported in proximity to any suitable scanner or vision system of the automated transport and positioning system 100 so that the location and identity of the workpiece 400 is verified (FIG. 8, Block 932). A status of the workpiece location or in process data of the workpiece is updated in the data structure based on the identification of the workpiece FIG. 8, Block 934). As may be realized, in one aspect, each workpiece has a predetermined microscopy process associated with it and the controller 199 sends processing data to, for example, the process module PM to effect processing of the workpiece 400 according to the predetermined microscopy process based on the identity of the workpiece. Process/analysis data (e.g. a location of the workpiece within the system 100, specimen images, specimen orientation, or any other suitable physical and/or analytical data) associated with each sample transferred to the processing module PM or processing performed on the sample is recorded in the data structure DS as described above (FIG. 8, Block 936). Following processing in the process module PM the samples held on the workpieces are returned to a respective cassette 102 by workpiece positioning unit 104 and the respective cassette 102 is returned to a respective magazine 105 by the workpiece or cassette shuttle 126 and a status of the workpiece is updated in the data structure DS through identification of the workpiece with any suitable scanner SCR or vision system of the automated transport and positioning system 100.

The magazine 105 is removed from the automated transport and positioning system 100 in any suitable manner such as by magazine transport unit 1001A. In one aspect, the magazine 105 is placed in storage 1069 by the magazine transport unit 1001A where the storage units 1069 include suitable vision systems 1069V, similar to those described herein, for communicating to the controller 199 a location of the magazine 105 within the storage unit 1069. In another aspect, the magazine is returned to a magazine loader 1002 where the cassettes 102 are removed and the cassettes are placed in a storage unit 1069 such that a location of the cassette 102 within the storage unit 1069 is communicated to the controller 199 by, for example, the vision system 1069V. In still other aspects, the magazines 102 are returned to the automated transport and positioning system 100 where the workpieces 400 are removed from the cassettes 102 (and in one aspect placed in storage) where the removal of the sample from the automated transport and positioning system 100 and cassettes 102 is communicated to the controller 199 in any suitable manner (such as through suitable sensors, optical readers, user interfaces, etc.) where the location of the sample is updated in the data structure DS (FIG. 8, Block 940).

As may be realized, the movement of the workpieces 400 (and specimen samples thereon) throughout the workpiece processing system or facility 100PS is effected by one or more drive axes of one or more transports of, for example, the automated transport 1001, the automated transport and positioning system 100, the workpiece sequencer modules 1099 or any other suitable workpiece transport as described in, for example, U.S. patent application Ser. No. 14/538,391 entitled "Workpiece Transport and Positioning Apparatus" and filed on Nov. 11, 2014 the disclosure of which is incorporated herein by reference in its entirety. Each of the drive axes provides data to the controller 199 regarding the position of the workpieces 400 (and the specimen samples thereon) to effect updating the status (e.g. location status, processing status, sequence status within a batch of workpieces, orientation status, etc.) of the workpiece in the data structure DS and/or laboratory information management system LIMS.

In one aspect the data structure provides a series of, for example, data points (formed from the process/analysis data obtained during sample analysis as described above) related to the sequenced order of a batch of samples for a common structure 1070. The controller 199 is, in one aspect, configured to provide an automated determination of a characteristic (e.g. a chemical makeup, a physical makeup, a status or health of biological tissue, a structural integrity of the structure, etc.) of the structure 1070 by analyzing the data points of each sample and providing a conclusion of the overall results for the analysis of the structure 1070 associated with the sequenced order of the batch of samples (FIG. 8, Block 945). As may be realized, the tracking of the samples of the structure 1070, with the data structure DS, from the creation of the samples and placement of the samples on a respective workpiece 400 to the conclusion of overall results for the structure (e.g. comprised of the samples) maintains the integrity of the overall structure 1070 during the automated analysis of each sample of the structure 1070.

Referring now to FIG. 9 the batch holding of the workpieces 400 includes providing the cassette 102 having a frame 102F and an array of grid holding receptacles (e.g. pockets 500) in the frame 102F, each of the pockets being configured to hold at least one workpiece 400 therein (FIG. 9, Block 1900). A readable data storage medium (as described above) is provided and connected to the cassette frame 102F where the readable data storage medium embodies a unique predetermined cassette frame characteristic (e.g. such the cassette identifiers described above) that corresponds to the cassette frame (FIG. 9, Block 1910). As described above, the readable data storage medium is representative of a predetermined workpiece characteristic of a workpiece held in the array of pockets 500 of the cassette 102. As also described above, the predetermined workpiece characteristic is representative of one or more of a source material configuration from which grid specimens of the grid array are made; holder (e.g. cassette) identification data that relates the magazine and grid array in the array of pockets to the source material configuration; and/or is workpiece identification data relating each workpiece and specimen disposed on the workpiece.

In accordance with one or more aspects of the disclosed embodiment an automated workpiece processing system includes at least one workpiece processing unit; a workpiece holder configured to removably hold a batch of workpieces therein, each workpiece embodying workpiece identifying indicia where the workpiece identifying indicia is a physical representation of a sample held on a respective workpiece, and to interface with the at least one automated workpiece processing unit; and a controller including a memory having a data structure therein that effects, with the workpiece identifying indicia, batch process tracking of each workpiece in the batch of workpieces through the at least one automated workpiece processing unit in a predetermined batch workpiece processing sequence.

In accordance with one or more aspects of the disclosed embodiment the workpiece identifying indicia embodies and the data structure includes at least one predetermined characteristic of the sample held on the respective workpiece.

In accordance with one or more aspects of the disclosed embodiment the at least one predetermined characteristic includes at least one or more of data regarding the processing of the sample before analysis of the sample, and data regarding results of sample analysis.

In accordance with one or more aspects of the disclosed embodiment the workpiece holder comprises an ordered sequence of samples held on the respective workpiece, where the ordered sequence is based on the workpiece identifying indicia.

In accordance with one or more aspects of the disclosed embodiment the workpiece processing unit comprises one or more of an electron microscope, and a workpiece holder storage.

In accordance with one or more aspects of the disclosed embodiment the workpiece holder is configured for insertion within the at least one workpiece processing unit.

In accordance with one or more aspects of the disclosed embodiment the workpiece holder comprises a frame configured to removably hold one or more workpiece holding cassettes where each workpiece holding cassette includes a grid of workpiece holding locations.

In accordance with one or more aspects of the disclosed embodiment each workpiece holding cassette comprises an ordered sequence of samples held on the workpieces in the workpiece holding locations, where the ordered sequence of samples is based on the workpiece identifying indicia.

In accordance with one or more aspects of the disclosed embodiment each workpiece holding cassette includes cassette identifying indicia thereon, the data structure correlating the cassette identifying indicia with the workpiece identifying indicia of the workpieces held in a respective workpiece holding cassette.

In accordance with one or more aspects of the disclosed embodiment more than one workpiece holding cassette comprises an ordered sequence of samples held on the workpieces in the workpiece holding locations, where the ordered sequence is based on the workpiece identifying indicia and the cassette identifying indicia.

In accordance with one or more aspects of the disclosed embodiment each workpiece holding location includes a workpiece retaining feature.

In accordance with one or more aspects of the disclosed embodiment each workpiece holding location is configured so that a workpiece is transferred to and from a respective workpiece holding location by automation or manually.

In accordance with one or more aspects of the disclosed embodiment each workpiece holding location is configured so that a workpiece holding cassette is transferred to and from a respective specimen holding location by automation or manually.

In accordance with one or more aspects of the disclosed embodiment each workpiece holding cassette includes a cover, the cover including retention features configured to removably secure the cover to the frame, and removably secure a respective workpiece holding cassette within the frame.

In accordance with one or more aspects of the disclosed embodiment a batch holder for electron microscope sample grids includes a frame; an array of grid holding receptacles disposed in the frame, each of which being configured for holding at least one grid therein; a readable data storage medium connected to the frame embodying a unique predetermined characteristic corresponding to the batch holder; wherein the data storage medium is representative of another predetermined characteristic of a grid array held in the array of grid holding receptacles of the batch holder.

In accordance with one or more aspects of the disclosed embodiment the other predetermined characteristic is unique and different than the predetermined characteristic of the batch holder.

In accordance with one or more aspects of the disclosed embodiment the other predetermined characteristic is related to a predetermined sequence of specimens on the grid array.

In accordance with one or more aspects of the disclosed embodiment the predetermined sequence is automatically defined coincident with loading of each grid of the grid array in the batch holder.

In accordance with one or more aspects of the disclosed embodiment the predetermined sequence corresponds to a predetermined arrangement of the grid array within the array of grid holding receptacles of the holder.

In accordance with one or more aspects of the disclosed embodiment the other predetermined characteristic corresponds to a predetermined arrangement of the grid array in the array of grid holding receptacles of the holder.

In accordance with one or more aspects of the disclosed embodiment the other predetermined characteristic is representative of a source material configuration from which grid specimens of the grid array are made.

In accordance with one or more aspects of the disclosed embodiment the predetermined characteristic is holder identification data that relates the holder and grid array in the array of grid holding receptacles of the holder to the source material configuration.

In accordance with one or more aspects of the disclosed embodiment the other predetermined characteristic is grid identification data relating each grid, of the grid array in the grid holding receptacles, and specimen disposed on the grid.

In accordance with one or more aspects of the disclosed embodiment an automated holder sequence station for the batch holder described above, the automated holder sequencing station including a holder placement station configured for holding the batch holder; a grid transport, having an end effector arranged to hold a grid on the transport, and a drive section arranged for transporting and placing the grid in a grid holding receptacle of the batch holder; a reader disposed to read the data storage medium of the holder in the holder placement station; and a processor communicably connected to the grid transport and reader, and configured to register the predetermined characteristic of the batch holder from data of the data storage medium read by the reader, and register grid related data defining the other predetermined characteristic of the grid array loaded in the array of grid holding receptacles of the batch holder.

In accordance with one or more aspects of the disclosed embodiment a method for batch processing workpieces includes placing at least a portion of at least one specimen on each workpiece in a batch of workpieces, where each workpiece embodies workpiece identifying indicia that is a physical representation of the portion of the specimen held on a respective workpiece; and tracking, with a data structure disposed in a memory of a controller, processing of each workpiece in the batch of workpieces through at least one automated workpiece processing unit in predetermined batch workpiece processing sequence based on the workpiece identifying indicia.

In accordance with one or more aspects of the disclosed embodiment the at least one workpiece processing unit comprises one or more of a workpiece storage unit, and an electron microscope.

In accordance with one or more aspects of the disclosed embodiment the processing of each workpiece includes one or more of: the placing of the portion of the at least one sample on each workpiece in the batch of workpieces; placing each workpiece in the batch of samples in at least one workpiece holding cassette; placing the at least one workpiece holding cassette in at least one cassette holding magazine; placing the at least one cassette holding magazine in an automated loading and positioning system of the at least one workpiece processing unit; processing one or more workpieces in the batch of workpieces through the at least one workpiece processing unit by cycling the one or more workpieces through the at least one workpiece processing unit; removing the at least one cassette holding magazine from the automated loading and positioning system of the at least one workpiece processing unit; removing the at least one workpiece holding cassette from the at least one cassette holding magazine; and storing the workpieces, holding a respective portion of the at least one sample thereon.

In accordance with one or more aspects of the disclosed embodiment the workpiece identifying indicia embodies and the data structure includes at least one predetermined characteristic of the sample held on the respective workpiece.

In accordance with one or more aspects of the disclosed embodiment the at least one predetermined characteristic includes one or more of data regarding the processing of the portion of the at least one sample before analysis of the portion of the at least one sample, and data regarding results of sample analysis.

In accordance with one or more aspects of the disclosed embodiment the method further includes arranging the portion of the at least one sample placed on each workpiece in the batch of workpieces in an ordered sequence based on the workpiece identifying indicia.

In accordance with one or more aspects of the disclosed embodiment the method further includes arranging the portion of the at least one sample placed on each workpiece in the batch of workpieces in an ordered sequence within at least one workpiece holding cassette based on the workpiece identifying indicia, wherein the data structure includes the ordered sequence.

In accordance with one or more aspects of the disclosed embodiment each workpiece holding cassette includes cassette identifying indicia thereon, the method further comprising correlating, with the data structure, the cassette identifying indicia with the workpiece identifying indicia of the workpieces held in a respective workpiece holding cassette.

In accordance with one or more aspects of the disclosed embodiment a workpiece storage system includes at least one cassette having a cassette frame including one or more cassette retention features; a magazine including a magazine frame forming cassette holding locations therein; and at least one cassette cover configured to retain workpieces within a respective cassette, the at least one cassette cover including one or more cover engagement features being configured to engage the one or more cassette retention features and retain the respective cassette within the cassette cover, and engage the magazine frame and retain the respective cassette within the magazine.

In accordance with one or more aspects of the disclosed embodiment the cassette frame includes one or more workpiece holding stations formed in the cassette frame, the one or more workpiece holding stations being configured to hold workpieces therein.

In accordance with one or more aspects of the disclosed embodiment the at least one cassette cover spans the one or more workpiece holding stations of the respective cassette.

In accordance with one or more aspects of the disclosed embodiment the magazine comprises a cover locking feature configured to selectively engage the one or more cover engagement features where when engaged the cover is retained within the magazine.

In accordance with one or more aspects of the disclosed embodiment the cover locking feature is configured so that when engaged with the one or more cover engagement features the respective cassette is movable relative to the cover.

In accordance with one or more aspects of the disclosed embodiment the cover locking feature is configured to substantially simultaneously engage or disengage the one or more cover engagement features of each cover located within the cassette holding locations.

In accordance with one or more aspects of the disclosed embodiment the magazine frame includes kinematic coupling features configured to engage automated magazine handling equipment.

In accordance with one or more aspects of the disclosed embodiment each cassette includes kinematic coupling features configured to engage automated cassette handling equipment.

In accordance with one or more aspects of the disclosed embodiment each cassette embodies cassette identifying indicia identifying each workpiece held by the cassette.

In accordance with one or more aspects of the disclosed embodiment the cassette holding locations and the at least one cassette are configured so that the at least one cassette is placed within a respective cassette holding location in a single predetermined orientation relative to the magazine.

In accordance with one or more aspects of the disclosed embodiment the workpiece holder includes a frame; a two dimensional array of workpiece holding pockets disposed in the frame; and kinematic handling features disposed on the frame, the kinematic handling features being configured to engage an automated workpiece holder end effector and having a predetermined location relative to each of the workpiece holding pockets.

In accordance with one or more aspects of the disclosed embodiment the kinematic handling features provide relative positioning between each of the workpiece holding pockets and an automated workpiece end effector.

In accordance with one or more aspects of the disclosed embodiment the frame embodies indicia identifying a location of each workpiece holding pocket with the two dimensional array of workpiece holding pockets.

In accordance with one or more aspects of the disclosed embodiment the workpiece holder further includes a cover having a cover frame being shaped so that at least a portion of the frame fits into the cover frame and a portion of the cover spans the two dimensional array of workpiece holding pockets.

In accordance with one or more aspects of the disclosed embodiment the cover frame includes frame retention features and the frame includes mating retention features configured to engage the frame retention features for securing the frame within the cover.

In accordance with one or more aspects of the disclosed embodiment the frame includes a first surface and a second surface that opposes the first surface, the kinematic handling features being located on the first surface, the workpiece holder further comprising gripping features on the second surface in an opposing relationship with the kinematic handling features.

In accordance with one or more aspects of the disclosed embodiment the workpiece holder further includes a wireless identification module mounted to the frame, the wireless identification module being configured to convey one or more of an identification of the frame and the workpieces held in the workpiece holding pockets to an automation controller.

In accordance with one or more aspects of the disclosed embodiment the frame includes recessed gripping surfaces on one or more sides of the frame.

In accordance with one or more aspects of the disclosed embodiment batch holder for electron microscope sample grid cassettes includes a frame; an array of cassette holding receptacles disposed in the frame, each of which being configured for holding a sample grid cassette therein;

a readable data storage medium connected to the frame embodying a unique predetermined characteristic corresponding to the batch holder; wherein the data storage medium is representative of another predetermined characteristic of at least one sample grid cassette held in the array of cassette holding receptacles of the batch holder.

In accordance with one or more aspects of the disclosed embodiment the other predetermined characteristic is unique and different than the predetermined characteristic of the batch holder.

In accordance with one or more aspects of the disclosed embodiment the other predetermined characteristic is related to a predetermined sequence of specimens held on a grid array of the at least one sample grid cassette.

In accordance with one or more aspects of the disclosed embodiment the predetermined sequence is automatically associated with the batch holder coincident with loading of each sample grid cassette in the batch holder.

In accordance with one or more aspects of the disclosed embodiment the predetermined sequence corresponds to a predetermined arrangement of a grid array of the at least one sample grid cassette.

In accordance with one or more aspects of the disclosed embodiment the other predetermined characteristic corresponds to a predetermined arrangement of a grid array of the at least one sample grid cassette.

In accordance with one or more aspects of the disclosed embodiment the other predetermined characteristic is representative of a source material configuration from which grid specimens of a grid array of the at least one sample grid cassette are made.

In accordance with one or more aspects of the disclosed embodiment the predetermined characteristic is holder identification data that relates the batch holder and the grid array in the at least one sample grid cassette to the source material configuration.

In accordance with one or more aspects of the disclosed embodiment the other predetermined characteristic is grid identification data relating each grid, of a grid array of the at least one sample grid cassette, and specimen disposed on the grid.

In accordance with one or more aspects of the disclosed embodiment a method for batch holding electron microscope sample grids includes providing a cassette frame having an array of grid holding receptacles disposed in the cassette frame, each of which being configured for holding at least one grid therein; providing a readable data storage medium connected to the cassette frame embodying a unique predetermined cassette frame characteristic corresponding to the cassette frame; wherein the data storage medium is representative of a predetermined grid characteristic of a grid array held in the array of grid holding receptacles of the cassette frame.

In accordance with one or more aspects of the disclosed embodiment the predetermined grid characteristic is unique and different than the predetermined cassette frame characteristic.

In accordance with one or more aspects of the disclosed embodiment the predetermined grid characteristic is related to a predetermined sequence of specimens in the array of grid holding receptacles.

In accordance with one or more aspects of the disclosed embodiment the method further includes automatically defining the predetermined sequence coincident with loading of each grid in an array of grids in the array of grid holding receptacles.

In accordance with one or more aspects of the disclosed embodiment the predetermined sequence corresponds to a predetermined arrangement of the grid array within the array of grid holding receptacles of the holder.

In accordance with one or more aspects of the disclosed embodiment the predetermined grid characteristic corresponds to a predetermined arrangement of the grid array in the array of grid holding receptacles of the holder.

In accordance with one or more aspects of the disclosed embodiment the predetermined grid characteristic is representative of a source material configuration from which grid specimens of the grid array are made.

In accordance with one or more aspects of the disclosed embodiment the predetermined cassette frame characteristic is cassette identification data that relates the cassette frame and grid array in the array of grid holding receptacles of the cassette frame to the source material configuration.

In accordance with one or more aspects of the disclosed embodiment the predetermined grid characteristic is grid identification data relating each grid, of the grid array in the grid holding receptacles, and specimen disposed on the grid.

In accordance with one or more aspects of the disclosed embodiment the method further includes providing a magazine frame having an array of cassette frame holding receptacles disposed in the magazine frame, each of which being configured for holding the cassette frame therein; providing another readable data storage medium connected to the magazine frame embodying a unique predetermined magazine frame characteristic corresponding to the magazine frame; wherein the other data storage medium is associated with the predetermined grid characteristic.

In accordance with one or more aspects of the disclosed embodiment the predetermined magazine frame characteristic is unique and different than the predetermined cassette frame characteristic and the predetermined grid characteristic.

In accordance with one or more aspects of the disclosed embodiment the predetermined grid characteristic is related to a predetermined sequence of specimens held in the array of grid holding receptacles.

In accordance with one or more aspects of the disclosed embodiment the predetermined sequence is automatically associated with the magazine frame coincident with loading of each sample cassette frame in the magazine frame.

In accordance with one or more aspects of the disclosed embodiment an automated holder sequencing system for an electron microscope includes a batch holder including a frame; an array of grid holding receptacles disposed in the frame, each of which being configured for holding at least one grid therein; a readable data storage medium connected to the frame embodying a unique predetermined characteristic corresponding to the batch holder; wherein the data storage medium is representative of another predetermined characteristic of a grid array held in the array of grid holding receptacles of the batch holder; a holder placement station configured for holding the batch holder; a grid transport, having an end effector arranged to hold a grid on the transport, and a drive section arranged for transporting and placing the grid in a grid holding receptacle of the batch holder; a reader disposed to read the data storage medium of the holder in the holder placement station; and a processor communicably connected to the grid transport and reader, and configured to register the predetermined characteristic of the batch holder from data of the data storage medium read by the reader, and register grid related data defining the other predetermined characteristic of the grid array loaded in the array of grid holding receptacles of the batch holder.

In accordance with one or more aspects of the disclosed embodiment the other predetermined characteristic is unique and different than the predetermined characteristic of the batch holder.

In accordance with one or more aspects of the disclosed embodiment the other predetermined characteristic is related to a predetermined sequence of specimens on the grid array.

In accordance with one or more aspects of the disclosed embodiment the predetermined sequence is automatically defined coincident with loading of each grid of the grid array in the batch holder.

In accordance with one or more aspects of the disclosed embodiment the predetermined sequence corresponds to a predetermined arrangement of the grid array within the array of grid holding receptacles of the holder.

In accordance with one or more aspects of the disclosed embodiment the other predetermined characteristic corresponds to a predetermined arrangement of the grid array in the array of grid holding receptacles of the holder.

In accordance with one or more aspects of the disclosed embodiment wherein the other predetermined characteristic is representative of a source material configuration from which grid specimens of the grid array are made.

In accordance with one or more aspects of the disclosed embodiment the predetermined characteristic is holder identification data that relates the holder and grid array in the array of grid holding receptacles of the holder to the source material configuration.

In accordance with one or more aspects of the disclosed embodiment the other predetermined characteristic is grid identification data relating each grid, of the grid array in the grid holding receptacles, and specimen disposed on the grid.

In accordance with one or more aspects of the disclosed embodiment an electron microscopy system includes at least one batch grid processing station having a placement holding location for a grid batch holder and an automated grid transport configured for transporting and loading a batch of specimen grids in the batch holder; at least one electron microscope with another automated grid transport configured for automated transport of each grid of the grid batch in the batch holder for batch microscopy with the electron microscope; a processor communicably connected to the at least one batch grid processing station and the at least one electron microscope; wherein the processor is configured to automatically register a predetermined characteristic relating the grid batch holder to each grid in the grid batch holder and to an initial condition of the grid substantially coincident with loading of the grid batch in the batch holder.

In accordance with one or more aspects of the disclosed embodiment the processor is configured to register the predetermined characteristic and initial condition of the grid based on transport data from the automated grid transport.

In accordance with one or more aspects of the disclosed embodiment the processor is configured to register changes to the initial condition of the grid based on transport data from the other grid transport.

In accordance with one or more aspects of the disclosed embodiment the processor is configured to form a data structure corresponding to the predetermined characteristic of the holder embodying a condition of each grid of the grid batch in the batch holder.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the invention.

What is claimed is:

1. An automated workpiece processing system comprising:
    at least one workpiece processing unit;
    a workpiece holder configured
        to removably hold a batch of workpieces therein, each workpiece embodying workpiece identifying indicia that is distinct from the workpiece holder, where the workpiece identifying indicia is a physical representation of a sample held on a respective workpiece, and
        to interface with the at least one automated workpiece processing unit; and
    a controller including a memory having a data structure therein that effects, with the workpiece identifying indicia, batch process tracking of each workpiece in the batch distinct from other workpieces in the batch through the at least one automated workpiece processing unit in a predetermined batch workpiece processing sequence.

2. The automated workpiece processing system of claim 1, wherein the workpiece identifying indicia embodies and the data structure includes at least one predetermined characteristic of the sample held on the respective workpiece.

3. The automated workpiece processing system of claim 2, wherein the at least one predetermined characteristic includes at least one or more of
    data regarding the processing of the sample before analysis of the sample, and
    data regarding results of sample analysis.

4. The automated workpiece processing system of claim 1, wherein the workpiece holder comprises an ordered sequence of samples held on the respective workpiece, where the ordered sequence is based on the workpiece identifying indicia.

5. The automated workpiece processing system of claim 1, wherein the workpiece processing unit comprises one or more of
    an electron microscope, and
    a workpiece holder storage.

6. The automated workpiece processing system of claim 1, wherein the workpiece holder is configured for insertion within the at least one workpiece processing unit.

7. The automated workpiece processing system of claim 1, wherein the workpiece holder comprises a frame configured to removably hold one or more workpiece holding cassettes where each workpiece holding cassette includes a grid of workpiece holding locations.

8. The automated workpiece holding processing system of claim 7, wherein each workpiece holding cassette comprises an ordered sequence of samples held on the workpieces in the workpiece holding locations, where the ordered sequence of samples is based on the workpiece identifying indicia.

9. The automated workpiece processing system of claim 7, wherein each workpiece holding cassette includes cassette identifying indicia thereon, the data structure correlating the cassette identifying indicia with the workpiece identifying indicia of the workpieces held in a respective workpiece holding cassette.

10. The automated workpiece processing system of claim 9, wherein more than one workpiece holding cassette comprises an ordered sequence of samples held on the workpieces in the workpiece holding locations, where the ordered sequence is based on the workpiece identifying indicia and the cassette identifying indicia.

11. The automated workpiece processing system of claim 7, wherein each workpiece holding location includes a workpiece retaining feature.

12. The automated workpiece processing system of claim 7, wherein each workpiece holding location is configured so that a workpiece is transferred to and from a respective workpiece holding location by automation or manually.

13. The automated workpiece processing system of claim 7, wherein each workpiece holding location is configured so that a workpiece holding cassette is transferred to and from a respective specimen holding location by automation or manually.

14. The automated workpiece processing system of claim 7, wherein each workpiece holding cassette includes a cover, the cover including retention features configured to
  removably secure the cover to the frame, and
  removably secure a respective workpiece holding cassette within the frame.

15. A method for batch processing workpieces, the method comprising:
  placing at least a portion of at least one specimen on each workpiece in a batch of workpieces, where each workpiece embodies workpiece identifying indicia that is distinct from a workpiece holder holding the workpiece and the workpiece identifying indicia is a physical representation of the portion of the specimen held on a respective workpiece; and
  tracking, with a data structure disposed in a memory of a controller, processing of each workpiece in the batch distinct from other workpieces in the batch through at least one automated workpiece processing unit in predetermined batch workpiece processing sequence based on the workpiece identifying indicia.

16. The method of claim 15, wherein the at least one workpiece processing unit comprises one or more of
  a workpiece storage unit, and
  an electron microscope.

17. The method of claim 15, wherein the processing of each workpiece comprises one or more of:
  the placing of the portion of the at least one sample on each workpiece in the batch of workpieces;
  placing each workpiece in the batch of samples in at least one workpiece holding cassette;
  placing the at least one workpiece holding cassette in at least one cassette holding magazine;
  placing the at least one cassette holding magazine in an automated loading and positioning system of the at least one workpiece processing unit;
  processing one or more workpieces in the batch of workpieces through the at least one workpiece processing unit by cycling the one or more workpieces through the at least one workpiece processing unit;
  removing the at least one cassette holding magazine from the automated loading and positioning system of the at least one workpiece processing unit;
  removing the at least one workpiece holding cassette from the at least one cassette holding magazine; and
  storing the workpieces, holding a respective portion of the at least one sample thereon.

18. The method of claim 15, wherein the workpiece identifying indicia embodies and the data structure includes at least one predetermined characteristic of the sample held on the respective workpiece.

19. The method of claim 18, wherein the at least one predetermined characteristic includes one or more of
  data regarding the processing of the portion of the at least one sample before analysis of the portion of the at least one sample, and
  data regarding results of sample analysis.

20. The method of claim 15, further comprising arranging the portion of the at least one sample placed on each workpiece in the batch of workpieces in an ordered sequence based on the workpiece identifying indicia.

21. The method of claim 15, further comprising arranging the portion of the at least one sample placed on each workpiece in the batch of workpieces in an ordered sequence within at least one workpiece holding cassette based on the workpiece identifying indicia, wherein the data structure includes the ordered sequence.

22. The method of claim 21, wherein each workpiece holding cassette includes cassette identifying indicia thereon, the method further comprising correlating, with the data structure, the cassette identifying indicia with the workpiece identifying indicia of the workpieces held in a respective workpiece holding cassette.

* * * * *